(12) United States Patent
Lin et al.

(10) Patent No.: US 9,445,918 B1
(45) Date of Patent: Sep. 20, 2016

(54) EXPANDABLE SPINAL FUSION IMPLANTS AND RELATED INSTRUMENTS AND METHODS

(71) Applicant: NuVasive, Inc., San Diego, CA (US)

(72) Inventors: Erika Lin, San Diego, CA (US); Jeremy Malik, San Diego, CA (US); Ryan Donahoe, San Diego, CA (US); Christopher Stein, San Diego, CA (US); David Hannah, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 14/060,558

(22) Filed: Oct. 22, 2013

Related U.S. Application Data

(60) Provisional application No. 61/793,626, filed on Mar. 15, 2013, provisional application No. 61/717,003, filed on Oct. 22, 2012.

(51) Int. Cl.
*A61F 2/44* (2006.01)

(52) U.S. Cl.
CPC .................................. *A61F 2/4455* (2013.01)

(58) Field of Classification Search
CPC ...... A61F 2/4611; A61F 2/446; A61F 2/447; A61F 2/44; A61F 2/442; A61F 2/4455; A61F 2/4465
USPC ........................................... 623/17.11, 17.16
See application file for complete search history.

(56) References Cited

U.S. PATENT DOCUMENTS

| | | |
|---|---|---|
| 2,083,922 A | 6/1937 | Roessel |
| 2,647,512 A | 8/1953 | Johnson |
| 3,614,532 A | 10/1971 | Smith, Jr. et al. |
| 4,232,670 A | 11/1980 | Richter et al. |
| 4,671,263 A | 6/1987 | Draenert |
| 4,800,875 A | 1/1989 | Ray |
| 4,877,020 A | 10/1989 | Vich |
| 4,995,867 A | 2/1991 | Zollinger |
| 5,171,278 A | 12/1992 | Pisharodi |
| 5,235,966 A | 8/1993 | Jamner |
| 5,390,683 A | 2/1995 | Pisharodi |
| 5,514,135 A | 5/1996 | Earle |
| 5,522,899 A | 6/1996 | Michelson |
| 5,596,325 A | 1/1997 | Maas |
| 5,693,100 A | 12/1997 | Pisharodi |
| 5,702,454 A | 12/1997 | Baumgartner |
| 5,782,830 A | 7/1998 | Farris |
| 5,861,041 A | 1/1999 | Tienboon |
| 5,885,299 A | 3/1999 | Winslow et al. |
| 6,019,793 A | 2/2000 | Perren et al. |

(Continued)

FOREIGN PATENT DOCUMENTS

| | | |
|---|---|---|
| AU | 2005204244 A1 | 9/2005 |
| AU | 2001288840 B2 | 2/2008 |

(Continued)

*Primary Examiner* — Kevin T Truong
*Assistant Examiner* — Si Ming Ku
(74) *Attorney, Agent, or Firm* — Jeremy A. Smith; Bradley Arant Boult Cummings LLP

(57) ABSTRACT

A system for performing interbody fusion surgery including an expandable intervertebral spacer and specialized instruments for choosing the correct size of implant, implanting the device within the intervertebral space, and for delivery of bone graft or bone substitute to the interior of the implant.

7 Claims, 34 Drawing Sheets

(56) References Cited

U.S. PATENT DOCUMENTS

| | | |
|---|---|---|
| 6,039,761 A | 3/2000 | Li et al. |
| 6,110,210 A | 8/2000 | Norton et al. |
| 6,113,639 A | 9/2000 | Ray et al. |
| 6,179,873 B1 | 1/2001 | Zientek |
| 6,193,757 B1 | 2/2001 | Foley et al. |
| 6,200,347 B1 | 3/2001 | Anderson et al. |
| 6,206,923 B1 | 3/2001 | Boyd et al. |
| 6,241,734 B1 | 6/2001 | Scribner et al. |
| 6,251,140 B1 | 6/2001 | Marino et al. |
| 6,264,655 B1 | 7/2001 | Pisharodi |
| 6,280,456 B1 | 8/2001 | Scribner et al. |
| 6,296,149 B1 | 10/2001 | Long |
| 6,319,257 B1 | 11/2001 | Carignan et al. |
| 6,332,895 B1 | 12/2001 | Suddaby |
| 6,387,130 B1 | 5/2002 | Stone et al. |
| 6,436,140 B1 | 8/2002 | Liu et al. |
| 6,451,057 B1 | 9/2002 | Chen et al. |
| 6,468,311 B2 | 10/2002 | Boyd et al. |
| 6,488,710 B2 | 12/2002 | Besselink |
| 6,537,320 B1 | 3/2003 | Michelson |
| 6,558,424 B2 | 5/2003 | Thalgott |
| 6,582,438 B2 | 6/2003 | DeMayo |
| 6,613,089 B1 | 9/2003 | Estes et al. |
| 6,620,169 B1 | 9/2003 | Peterson et al. |
| 6,620,196 B1 | 9/2003 | Trieu |
| 6,676,663 B2 | 1/2004 | Higueras et al. |
| 6,676,665 B2 | 1/2004 | Foley et al. |
| 6,723,126 B1 | 4/2004 | Berry |
| 6,764,514 B1 | 7/2004 | Li et al. |
| 6,783,515 B1 | 8/2004 | Miller et al. |
| 6,824,564 B2 | 11/2004 | Crozet |
| 6,855,167 B2 | 2/2005 | Shimp et al. |
| 6,936,070 B1 | 8/2005 | Muhanna |
| 6,942,697 B2 | 9/2005 | Lange et al. |
| 6,986,772 B2 | 1/2006 | Michelson |
| 7,018,413 B2 | 3/2006 | Krüger |
| 7,037,339 B2 | 5/2006 | Houfburg |
| 7,070,598 B2 | 7/2006 | Lim et al. |
| 7,087,055 B2 | 8/2006 | Lim et al. |
| 7,097,648 B1 | 8/2006 | Globerman et al. |
| 7,115,132 B2 | 10/2006 | Errico et al. |
| 7,118,579 B2 | 10/2006 | Michelson |
| 7,128,760 B2 | 10/2006 | Michelson |
| 7,169,182 B2 | 1/2007 | Errico et al. |
| 7,196,907 B2 | 3/2007 | Zheng |
| 7,204,851 B2 | 4/2007 | Trieu et al. |
| 7,214,243 B2 | 5/2007 | Taylor |
| 7,226,453 B2 | 6/2007 | Chao et al. |
| 7,232,463 B2 | 6/2007 | Falahee |
| 7,267,690 B2 | 9/2007 | Felt |
| 7,318,839 B2 | 1/2008 | Malberg et al. |
| 7,325,702 B2 | 2/2008 | Lu |
| 7,326,216 B2 | 2/2008 | Bertagnoli et al. |
| 7,371,241 B2 | 5/2008 | Evans et al. |
| 7,431,735 B2 | 10/2008 | Liu et al. |
| 7,442,210 B2 | 10/2008 | Segal et al. |
| 7,507,241 B2 | 3/2009 | Levy et al. |
| 7,513,900 B2 | 4/2009 | Carrison et al. |
| 7,572,263 B2 | 8/2009 | Preissman |
| 7,575,577 B2 | 8/2009 | Boyd et al. |
| 7,601,157 B2 | 10/2009 | Boyd et al. |
| 7,621,956 B2 | 11/2009 | Paul et al. |
| 7,632,312 B2 | 12/2009 | Leclercq |
| 7,641,664 B2 | 1/2010 | Pagano |
| 7,641,690 B2 | 1/2010 | Abdou |
| 7,682,394 B2 | 3/2010 | Recoules-Arche et al. |
| 7,690,381 B2 | 4/2010 | Bartish, Jr. et al. |
| 7,727,279 B2 | 6/2010 | Zipnick et al. |
| 7,731,751 B2 | 6/2010 | Butler et al. |
| 7,753,958 B2 | 7/2010 | Gordon et al. |
| 7,799,056 B2 | 9/2010 | Sankaran |
| 7,803,159 B2 | 9/2010 | Perez-Cruet et al. |
| 7,823,938 B2 | 11/2010 | McKee et al. |
| 7,850,734 B2 | 12/2010 | Oh et al. |
| 7,854,766 B2 | 12/2010 | Moskowitz et al. |
| 7,857,818 B2 | 12/2010 | Trieu et al. |
| 7,862,617 B2 | 1/2011 | Lamprich et al. |
| 7,879,095 B2 | 2/2011 | Pisharodi |
| 7,879,103 B2 | 2/2011 | Gertzman et al. |
| 7,883,512 B2 | 2/2011 | Pajunk et al. |
| 7,887,589 B2 | 2/2011 | Glenn et al. |
| 7,887,593 B2 | 2/2011 | McKay et al. |
| 7,901,409 B2 | 3/2011 | Canaveral et al. |
| 7,905,920 B2 | 3/2011 | Galea |
| 7,918,874 B2 | 4/2011 | Siegal |
| 7,947,078 B2 | 5/2011 | Siegal |
| 7,951,199 B2 | 5/2011 | Miller |
| 7,959,676 B2 | 6/2011 | Thramann et al. |
| 7,988,735 B2 | 8/2011 | Yurek et al. |
| 8,002,831 B2 | 8/2011 | Burd et al. |
| 8,002,833 B2 | 8/2011 | Fabris Monterumici et al. |
| 8,007,532 B2 | 8/2011 | Manders |
| 8,007,535 B2 | 8/2011 | Hudgins et al. |
| 8,021,429 B2 | 9/2011 | Viker |
| 8,025,697 B2 | 9/2011 | Mcclellan, Iii et al. |
| 8,034,034 B2 | 10/2011 | Hess et al. |
| 8,034,109 B2 | 10/2011 | Zwirkoski |
| 8,043,376 B2 | 10/2011 | Falahee |
| 8,043,381 B2 | 10/2011 | Hestad et al. |
| 8,062,303 B2 | 11/2011 | Berry et al. |
| 8,062,373 B2 | 11/2011 | Fabian, Jr. |
| 8,088,147 B2 | 1/2012 | Ainsworth et al. |
| 8,100,916 B2 | 1/2012 | Kumar et al. |
| 8,105,382 B2 | 1/2012 | Olmos et al. |
| 8,137,401 B2 | 3/2012 | Stad et al. |
| 8,163,026 B2 | 4/2012 | Gray |
| 8,206,423 B2 | 6/2012 | Siegal |
| 8,241,358 B2 | 8/2012 | Butler et al. |
| 8,246,622 B2 | 8/2012 | Siegal et al. |
| 8,267,939 B2 | 9/2012 | Cipoletti et al. |
| 8,317,798 B2 | 11/2012 | Lim et al. |
| 8,317,866 B2 | 11/2012 | Palmatier et al. |
| 8,323,344 B2 | 12/2012 | Galley et al. |
| 8,328,818 B1 | 12/2012 | Seifert et al. |
| 8,328,852 B2 | 12/2012 | Zehavi et al. |
| 8,357,167 B2 | 1/2013 | Errico et al. |
| 8,377,137 B2 | 2/2013 | Sournac et al. |
| 8,409,291 B2 | 4/2013 | Blackwell et al. |
| 8,439,930 B2 | 5/2013 | Campion et al. |
| 8,465,524 B2 | 6/2013 | Siegal |
| 8,480,748 B2 | 7/2013 | Poulos |
| 8,486,147 B2 | 7/2013 | De Villiers et al. |
| 8,486,148 B2 | 7/2013 | Butler et al. |
| 8,486,149 B2 | 7/2013 | Saidha et al. |
| 8,512,348 B2 | 8/2013 | Chabansky et al. |
| 8,540,723 B2 | 9/2013 | Shadduck et al. |
| 8,551,173 B2 | 10/2013 | Lechmann et al. |
| 8,562,620 B2 | 10/2013 | Truckai et al. |
| 8,608,750 B2 | 12/2013 | Faccioli et al. |
| 8,613,771 B2 | 12/2013 | Hansell et al. |
| 8,613,773 B2 | 12/2013 | Barrett |
| 8,628,576 B2 | 1/2014 | Triplett et al. |
| 8,632,591 B2 | 1/2014 | Vila et al. |
| 8,636,803 B2 | 1/2014 | Hibri et al. |
| 8,663,331 B2 | 3/2014 | Mcclellan, Iii et al. |
| 8,672,977 B2 | 3/2014 | Siegal et al. |
| 8,685,095 B2 | 4/2014 | Miller et al. |
| 8,696,678 B2 | 4/2014 | Foster |
| 8,747,473 B2 | 6/2014 | Burd et al. |
| 8,777,993 B2 | 7/2014 | Siegal et al. |
| 8,778,027 B2 | 7/2014 | Medina |
| 8,795,375 B2 | 8/2014 | Malberg |
| 8,808,385 B1 | 8/2014 | Smith et al. |
| 8,828,018 B2 | 9/2014 | Ragab et al. |
| 8,840,648 B2 | 9/2014 | Tsuang et al. |
| 8,845,735 B2 | 9/2014 | Razian et al. |
| 8,870,959 B2 | 10/2014 | Arnin |
| 8,932,355 B2 | 1/2015 | Grotz et al. |
| 8,986,386 B2 | 3/2015 | Oglaza et al. |
| 8,986,388 B2 | 3/2015 | Siegal et al. |
| 8,992,618 B2 | 3/2015 | Lechmann et al. |
| 9,011,545 B2 | 4/2015 | Nakamura et al. |
| 9,044,333 B2 | 6/2015 | Puno |
| 9,044,334 B2 | 6/2015 | Siegal et al. |

(56) References Cited

U.S. PATENT DOCUMENTS

| | | | |
|---|---|---|---|
| 9,050,194 B2 | 6/2015 | Thibodeau | |
| 9,060,877 B2 | 6/2015 | Kleiner | |
| 9,066,809 B2 | 6/2015 | Hansell et al. | |
| 9,066,813 B2 | 6/2015 | Farris et al. | |
| 2002/0106393 A1 | 8/2002 | Bianchi et al. | |
| 2003/0004574 A1 | 1/2003 | Ferree | |
| 2003/0176924 A1 | 9/2003 | Burdett | |
| 2003/0220650 A1 | 11/2003 | Major et al. | |
| 2004/0010318 A1 | 1/2004 | Ferree | |
| 2004/0068234 A1 | 4/2004 | Martin et al. | |
| 2004/0133280 A1 | 7/2004 | Trieu | |
| 2004/0193154 A1 | 9/2004 | Leatherbury et al. | |
| 2004/0249459 A1 | 12/2004 | Ferree | |
| 2004/0267272 A1 | 12/2004 | Henniges et al. | |
| 2005/0071010 A1 | 3/2005 | Crozet | |
| 2005/0113762 A1 | 5/2005 | Kay et al. | |
| 2005/0131417 A1 | 6/2005 | Ahern et al. | |
| 2005/0222681 A1 | 10/2005 | Richley et al. | |
| 2005/0228397 A1 | 10/2005 | Malandain et al. | |
| 2005/0256576 A1 | 11/2005 | Moskowitz et al. | |
| 2005/0283245 A1 | 12/2005 | Gordon et al. | |
| 2006/0036241 A1 | 2/2006 | Siegal | |
| 2006/0069441 A1 | 3/2006 | Zucherman et al. | |
| 2006/0078423 A1 | 4/2006 | Zheng | |
| 2006/0106462 A1 | 5/2006 | Tsou | |
| 2006/0142858 A1 | 6/2006 | Colleran et al. | |
| 2006/0195191 A1 | 8/2006 | Sweeney et al. | |
| 2006/0235423 A1 | 10/2006 | Cantu | |
| 2006/0253202 A1 | 11/2006 | Lipov | |
| 2006/0265077 A1 | 11/2006 | Zwirkoski | |
| 2007/0010845 A1 | 1/2007 | Gong et al. | |
| 2007/0043376 A1 | 2/2007 | Leatherbury et al. | |
| 2007/0055300 A1 | 3/2007 | Osorio et al. | |
| 2007/0067034 A1 | 3/2007 | Chirico et al. | |
| 2007/0093689 A1 | 4/2007 | Steinberg | |
| 2007/0093906 A1 | 4/2007 | Hudgins et al. | |
| 2007/0118222 A1 | 5/2007 | Lang | |
| 2007/0161962 A1 | 7/2007 | Edie et al. | |
| 2007/0162135 A1 | 7/2007 | Segal et al. | |
| 2007/0168043 A1 | 7/2007 | Ferree | |
| 2007/0173939 A1 | 7/2007 | Kim et al. | |
| 2007/0233244 A1 | 10/2007 | Lopez et al. | |
| 2007/0233272 A1 | 10/2007 | Boyce et al. | |
| 2007/0260258 A1 | 11/2007 | Sommerich | |
| 2007/0260314 A1 | 11/2007 | Biyani | |
| 2007/0260318 A1 | 11/2007 | Lawson | |
| 2008/0039855 A1 | 2/2008 | Lambert | |
| 2008/0039942 A1 | 2/2008 | Bergeron | |
| 2008/0051707 A1 | 2/2008 | Phan et al. | |
| 2008/0065221 A1 | 3/2008 | Alleyne et al. | |
| 2008/0103597 A1 | 5/2008 | Lechmann et al. | |
| 2008/0119853 A1 | 5/2008 | Felt et al. | |
| 2008/0161933 A1 | 7/2008 | Grotz et al. | |
| 2008/0183204 A1 | 7/2008 | Greenhalgh et al. | |
| 2008/0195156 A1 | 8/2008 | Ainsworth et al. | |
| 2008/0195210 A1 | 8/2008 | Milijasevic et al. | |
| 2008/0208345 A1 | 8/2008 | Hurlbert et al. | |
| 2008/0228192 A1 | 9/2008 | Beyar et al. | |
| 2008/0243130 A1 | 10/2008 | Paris et al. | |
| 2008/0249628 A1 | 10/2008 | Altarac et al. | |
| 2008/0281346 A1 | 11/2008 | Greenhalgh et al. | |
| 2008/0281364 A1 | 11/2008 | Chirico et al. | |
| 2009/0008360 A1 | 1/2009 | Piccioli et al. | |
| 2009/0062422 A1 | 3/2009 | Nakamura et al. | |
| 2009/0076607 A1 | 3/2009 | Aalsma et al. | |
| 2009/0082872 A1 | 3/2009 | Beger | |
| 2009/0093882 A1 | 4/2009 | Oh et al. | |
| 2009/0099569 A1 | 4/2009 | Beger | |
| 2009/0131867 A1 | 5/2009 | Liu et al. | |
| 2009/0131950 A1 | 5/2009 | Liu et al. | |
| 2009/0157186 A1 | 6/2009 | Magerl | |
| 2009/0222018 A1 | 9/2009 | Sidler | |
| 2009/0234454 A1 | 9/2009 | Siegal | |
| 2009/0248092 A1 | 10/2009 | Bellas et al. | |
| 2009/0270873 A1 | 10/2009 | Fabian | |
| 2009/0281628 A1 | 11/2009 | Oglaza et al. | |
| 2009/0292323 A1 | 11/2009 | Chirico et al. | |
| 2009/0299378 A1 | 12/2009 | Knopp | |
| 2009/0326543 A1 | 12/2009 | Fabian, Jr. | |
| 2010/0010633 A1 | 1/2010 | Kohm | |
| 2010/0114107 A1 | 5/2010 | Trieu | |
| 2010/0168858 A1 | 7/2010 | Hardenbrook et al. | |
| 2010/0268344 A1 | 10/2010 | De Villiers et al. | |
| 2011/0009969 A1 | 1/2011 | Puno | |
| 2011/0046740 A1 | 2/2011 | Chen et al. | |
| 2011/0066192 A1 | 3/2011 | Frasier et al. | |
| 2011/0125270 A1 | 5/2011 | Paul et al. | |
| 2011/0230965 A1 | 9/2011 | Schell et al. | |
| 2011/0251689 A1 | 10/2011 | Seifert et al. | |
| 2011/0276141 A1 | 11/2011 | Caratsch | |
| 2011/0320000 A1 | 12/2011 | O'Neil et al. | |
| 2012/0004732 A1 | 1/2012 | Goel et al. | |
| 2012/0083887 A1 | 4/2012 | Purcell et al. | |
| 2012/0083889 A1 | 4/2012 | Purcell et al. | |
| 2012/0089231 A1 | 4/2012 | Prestigiacomo | |
| 2012/0123546 A1* | 5/2012 | Medina | 623/17.16 |
| 2012/0143334 A1 | 6/2012 | Boyce et al. | |
| 2012/0209386 A1* | 8/2012 | Triplett et al. | 623/17.16 |
| 2012/0215316 A1 | 8/2012 | Mohr et al. | |
| 2012/0232660 A1 | 9/2012 | Davenport | |
| 2012/0277754 A1 | 11/2012 | Lin et al. | |
| 2012/0290094 A1 | 11/2012 | Lim et al. | |
| 2012/0296433 A1 | 11/2012 | Farin | |
| 2012/0310048 A1 | 12/2012 | Siegal et al. | |
| 2013/0041471 A1* | 2/2013 | Siegal et al. | 623/17.16 |
| 2013/0079882 A1 | 3/2013 | Wolfe et al. | |
| 2013/0103156 A1* | 4/2013 | Packer et al. | 623/17.16 |
| 2013/0138214 A1 | 5/2013 | Greenhalgh et al. | |
| 2013/0144387 A1 | 6/2013 | Walker et al. | |
| 2013/0158668 A1 | 6/2013 | Nichols et al. | |
| 2013/0173004 A1 | 7/2013 | Greenhalgh et al. | |
| 2013/0184822 A1 | 7/2013 | Kleiner | |
| 2013/0184823 A1 | 7/2013 | Malberg | |
| 2013/0190876 A1 | 7/2013 | Drochner et al. | |
| 2013/0190877 A1* | 7/2013 | Medina | 623/17.16 |
| 2013/0197648 A1 | 8/2013 | Boehm et al. | |
| 2013/0274883 A1 | 10/2013 | Mcluen et al. | |
| 2013/0325128 A1* | 12/2013 | Perloff et al. | 623/17.16 |
| 2014/0031940 A1 | 1/2014 | Banouskou | |
| 2014/0052253 A1 | 2/2014 | Perloff et al. | |
| 2014/0188224 A1 | 7/2014 | Dmuschewsky | |
| 2014/0194992 A1 | 7/2014 | Medina | |
| 2014/0277490 A1 | 9/2014 | Perloff et al. | |
| 2014/0358246 A1 | 12/2014 | Levy et al. | |
| 2015/0112436 A1 | 4/2015 | Siegal et al. | |

FOREIGN PATENT DOCUMENTS

| | | |
|---|---|---|
| AU | 2008202235 A1 | 6/2008 |
| CN | 101972179 A | 2/2011 |
| DE | 19710392 C1 | 3/1997 |
| EP | 0515912 A2 | 10/1996 |
| EP | 1043002 A2 | 10/2000 |
| EP | 1941847 A1 | 7/2008 |
| EP | 1980222 A1 | 10/2008 |
| EP | 2446860 A1 | 5/2012 |
| EP | 2526882 A1 | 11/2012 |
| EP | 2724915 A1 | 6/2014 |
| FR | 2900814 A1 | 11/2007 |
| FR | 2951370 A1 | 11/2007 |
| FR | 2913331 A1 | 9/2008 |
| IN | 2108MUM2008 | 4/2010 |
| JP | 2006223667 A | 8/2006 |
| JP | 201058345 A | 7/2010 |
| KR | 20020042627 A | 6/2002 |
| TW | 200724115 A | 7/2007 |
| WO | WO-9214423 A1 | 9/1992 |
| WO | WO-2005089679 A1 | 9/2005 |
| WO | WO-2006072941 A2 | 7/2006 |
| WO | WO-2007008568 A2 | 1/2007 |
| WO | WO-2007009107 A2 | 1/2007 |
| WO | WO-2007048252 A2 | 5/2007 |
| WO | WO-2007076377 A2 | 7/2007 |
| WO | WO-2008088139 A1 | 7/2008 |

(56) References Cited

FOREIGN PATENT DOCUMENTS

| WO | WO-2008132322 A2 | 11/2008 |
| WO | WO-2010008353 A1 | 1/2010 |
| WO | WO-2010092613 A1 | 8/2010 |
| WO | WO-2012065753 A1 | 5/2012 |
| WO | WO-2012115631 A1 | 8/2012 |
| WO | WO-2014091029 A1 | 6/2014 |

* cited by examiner

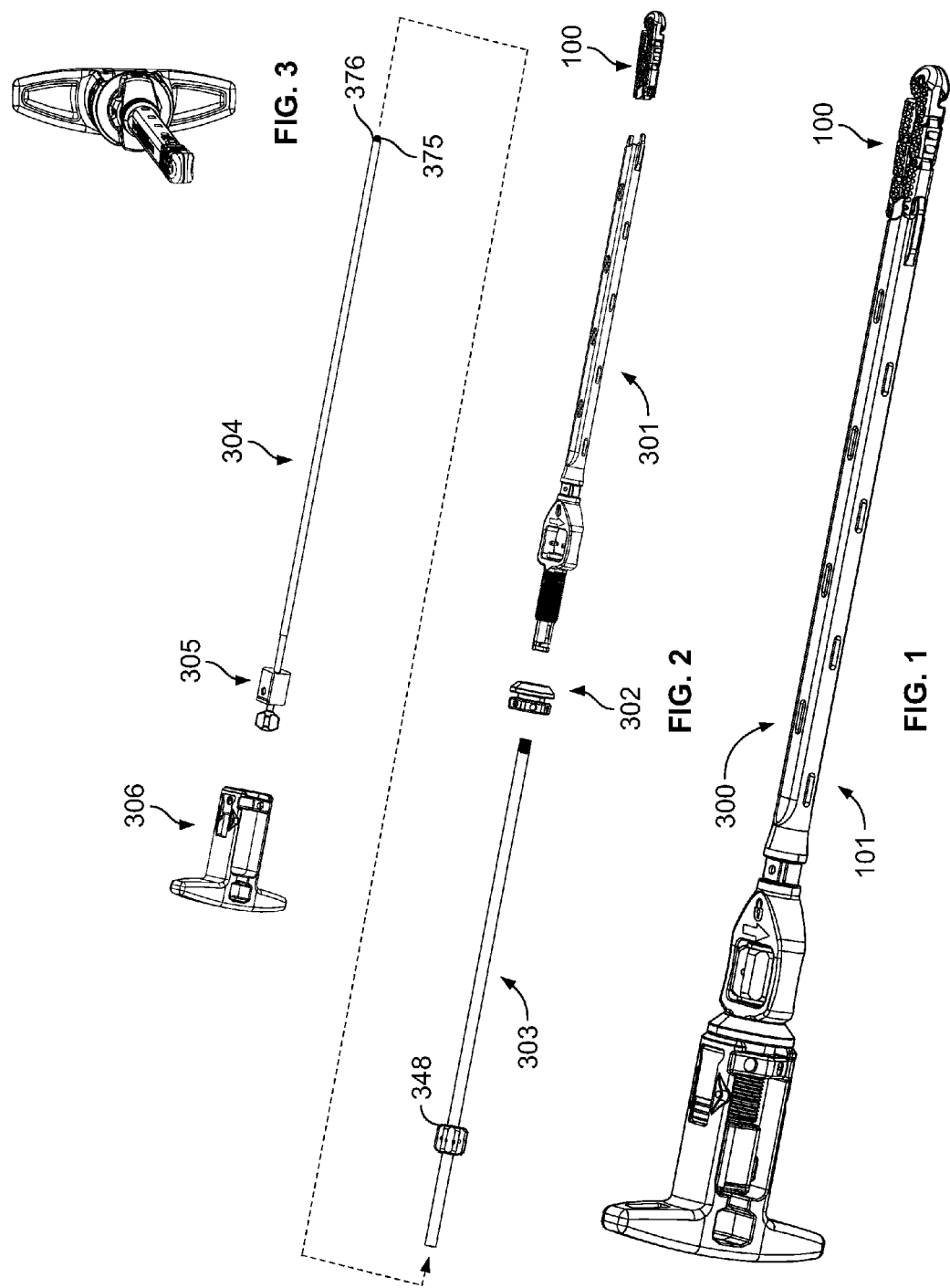

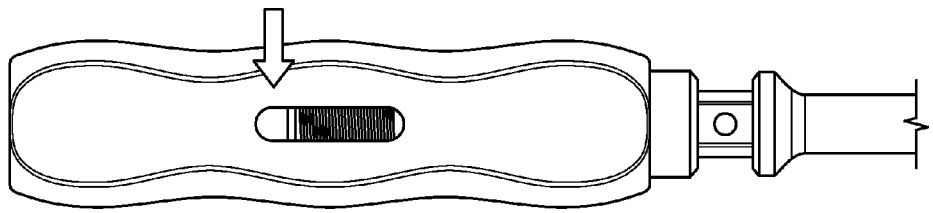
FIG. 83
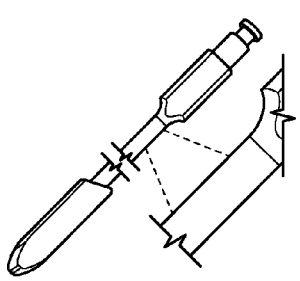 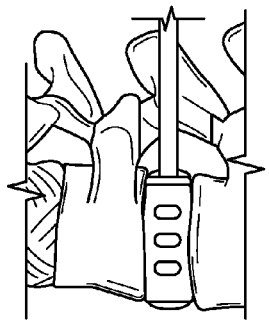
FIG. 84A  FIG. 84B
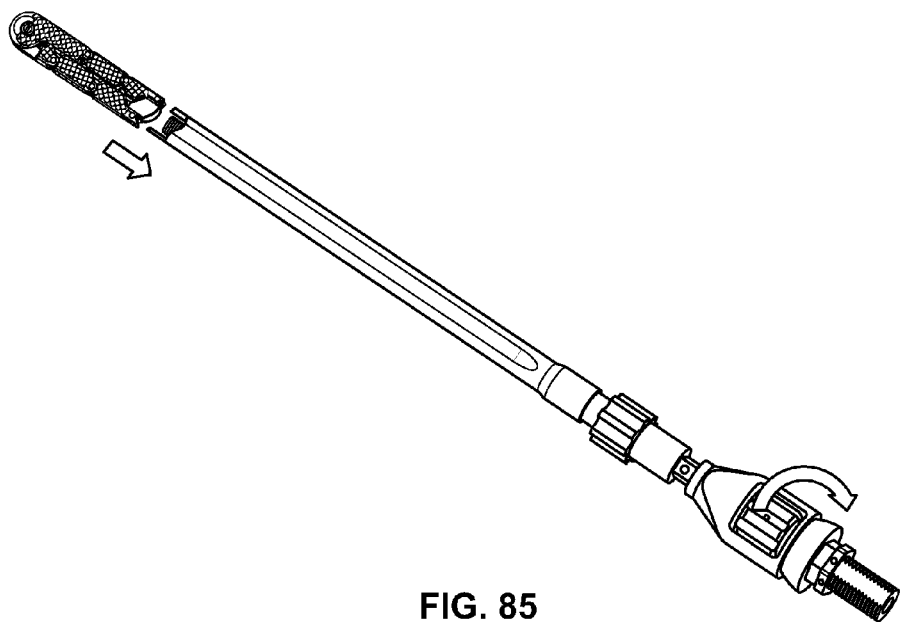
FIG. 85

EXPANDABLE SPINAL FUSION IMPLANTS AND RELATED INSTRUMENTS AND METHODS

CROSS REFERENCE TO RELATED APPLICATIONS

This application claims the benefit of the filing date of U.S. Provisional Patent Application Nos. 61/717,003, which was filed on Oct. 22, 2012, and 61/793,626 which was filed on Mar. 15, 2013. The contents of U.S. Application Nos. 61/717,003 and 61/793,626 are incorporated by reference as part of this application.

FIELD

This application relates generally to an intervertebral spacer and specialized instruments for choosing the correct size of implant, implanting the device within the intervertebral space, and for delivery of bone graft or bone substitute to the interior of the implant.

SUMMARY

The implant utilizes a plurality of joints between links of interbody spacer segments which in an insertion configuration assumes a collapsed elongate form for minimally invasive insertion down a narrow surgical corridor. The device expands to a larger footprint size in an implanted or expanded configuration at the predetermined site. In the implanted configuration, the implant is roughly the profile of the removed intervertebral disc and therein provides spacer support near the periphery of the endplate where the vertebral bone is most dense. In addition, in the implanted configuration, the spacer links define a large central aperture for packing of graft material.

A spacer template is disclosed to assist the surgeon is choosing the correct implant size but also to help validate that the disc space has been properly prepared through removal of soft tissue that may impede the final spacer from transitioning to the expanded configuration. The implant and instruments include a system and method for the insertion of the device and for the controlled transition from the insertion configuration to the implanted configuration once the device is presented in its predetermined location between the vertebral bodies. This includes mechanisms for controlling the profile of the links to prevent formation into undesired profiles in the intervertebral space and mechanisms to maintain a preferred shape once the device reaches a fully implanted configuration.

The insertion instrument also shares a minimally invasive elongated profile for use down a narrow surgical path. This instrument not only serves to attach, control and steer the implant into its predetermined location, it also controls the device's transition from the insertion configuration to the expanded implanted configuration and comprises features to prevent over expansion of the device. In addition, the instrument comprises features for attachment of a bone graft administration device and for directing the bone graft down a cannula in the instrument into the bone graft aperture defined by the expanded spacer links between the endplates. In cases in which the surgeon desires to remove the device after implantation, the instrument is also configured for reattachment and for transitioning the implant device from an implanted configuration back to an insertion configuration. Methods for implant size selection, implant insertion, transition to an implanted configuration, bone graft administration, and removal are disclosed in detail in later paragraphs.

In a preferred form, the implant device is well suited for minimally invasive insertion into the intervertebral space through a transforaminal surgical approach.

BRIEF DESCRIPTION OF THE DRAWINGS

FIG. 1 is a front perspective view of an exemplary embodiment of an inserter attached to an expandable implant in its insertion configuration.

FIG. 2 is a partially exploded perspective view of the implant and inserter illustrated in FIG. 1.

FIG. 3 is a distal end perspective view of the implant and inserter illustrated in FIG. 1.

FIG. 83 illustrates full expansion of a spacer template as indicated on the handle by the arrow pointing to green indicator is proximal to the slot.

FIG. 84A illustrates a paddle sizer.

FIG. 84B illustrates use of a paddle sizer inserted in the disc space.

FIG. 85 illustrates sliding spacer on to the control arms of the insertion instrument and advancing fixation tube threads to secure spacer to the insertion instrument.

DETAILED DESCRIPTION OF THE PREFERRED EMBODIMENTS

Figure 4:
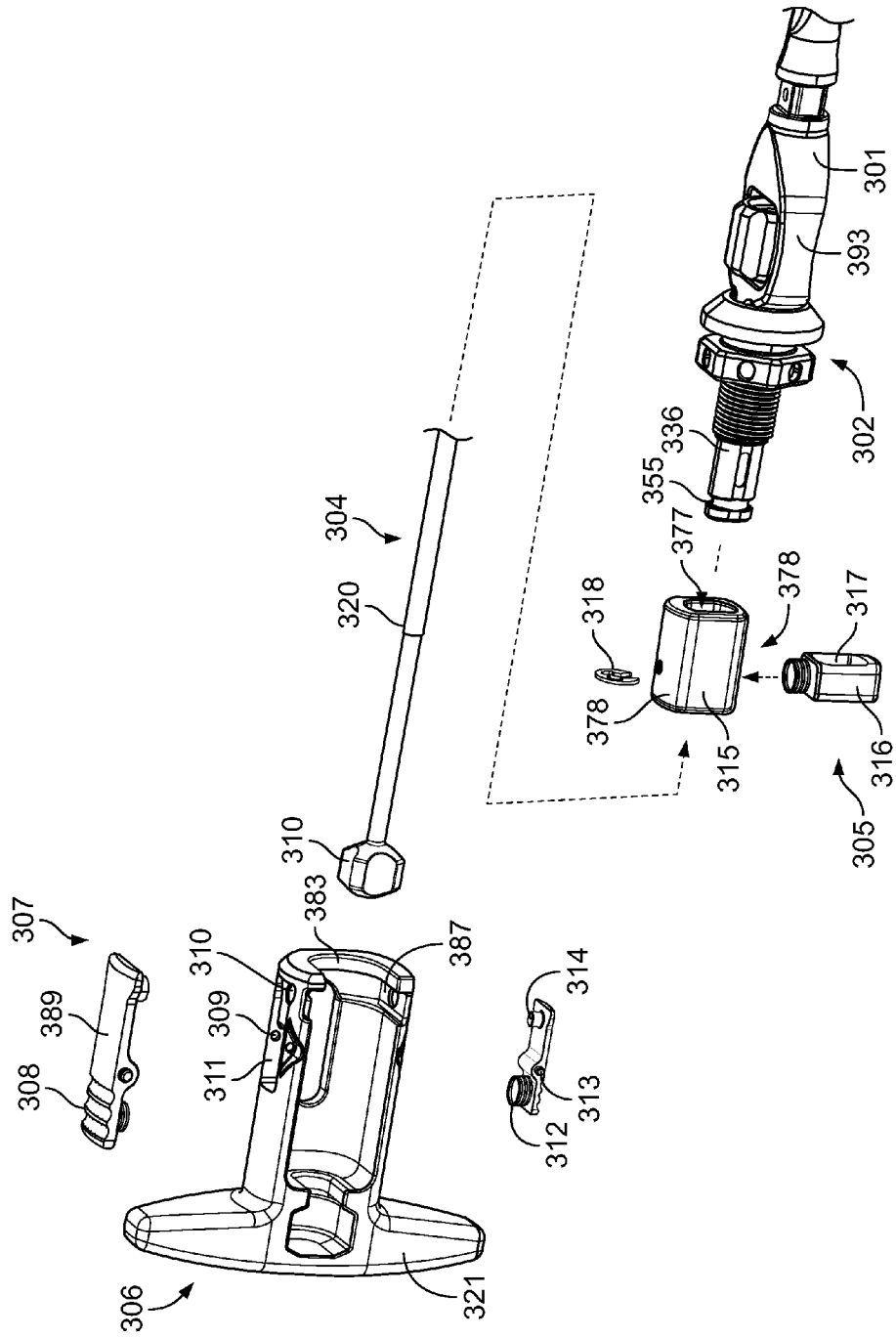
FIG. 4 is a partially exploded perspective view of the proximal end of the inserter illustrated in FIG. 1.

FIG. 1 illustrates an exemplary embodiment of an expandable spacer and insertion assembly 101 with the spacer 100 in its insertion configuration and mounted to spacer inserter 300. FIG. 2 illustrates a partially exploded view of each portion of assembly 101 including spacer 100, control frame 301, handle collar 302, fixation tube 303, expansion rod 304, expansion limiter 305, and expansion handle 306. FIG. 3 is a distal end view of assembly 101 illustrating the small diameter profile when assembly 101 is in its insertion configuration.

Figure 5:
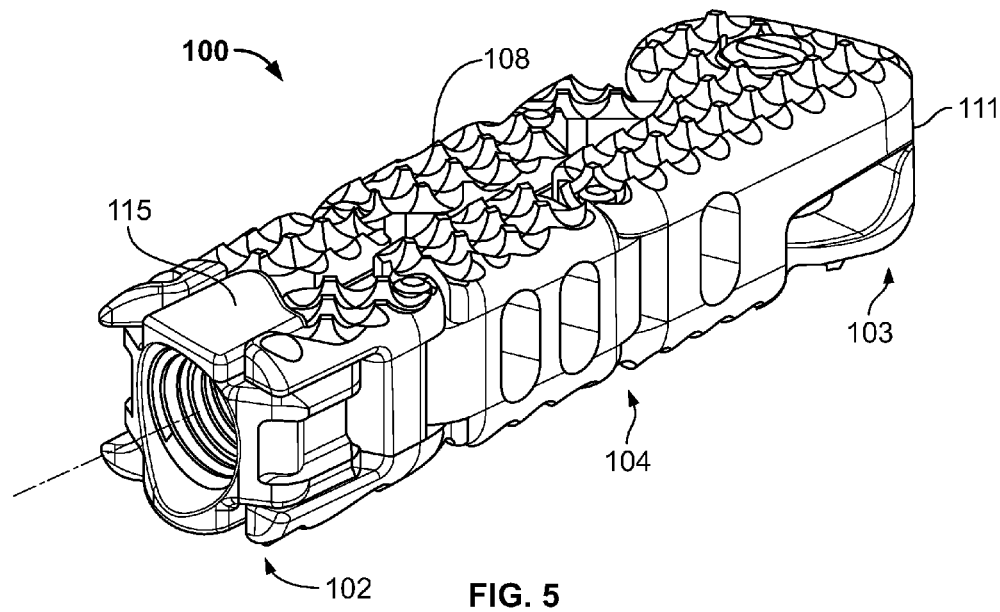
FIG. 5 is a proximal end perspective view of an exemplary embodiment of an expandable interbody implant in its insertion configuration.
Figure 6:
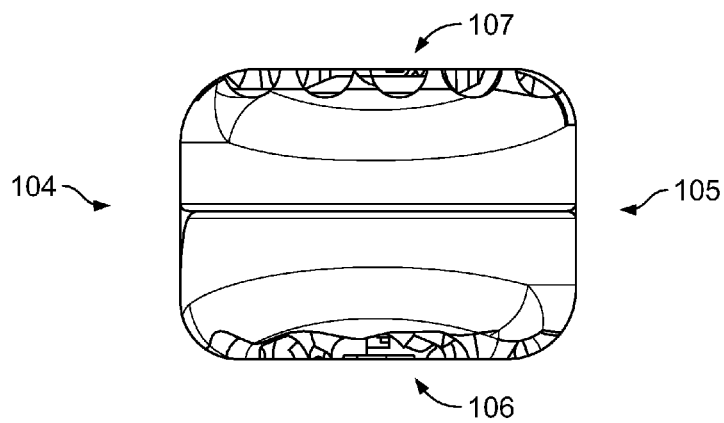
FIG. 6 is a lead end view of the expandable implant illustrated in FIG. 5.
Figure 7:
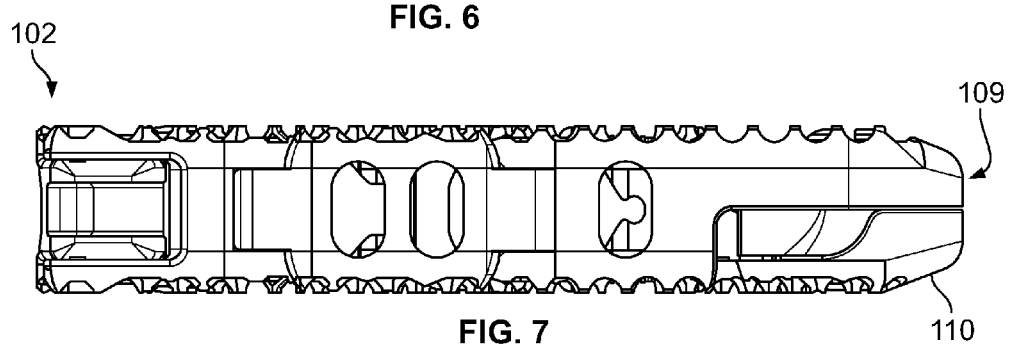
FIG. 7 is a side view of the expandable implant illustrated in FIG. 5.

A closer view of spacer 100 in its insertion configuration is illustrated in FIG. 5-7. The spacer 100 comprises a proximal end 102, a distal end 103, a lateral side 104, a medial side 105, and support face 107 with opposing support face 106. Teeth 108 are inscribed on support face 106 and support face 107 and are configured to embed in the superior and inferior vertebral endplates to prevent migration of spacer 100 once the spacer is placed in its predetermined location between the vertebral bodies.

Figure 15:
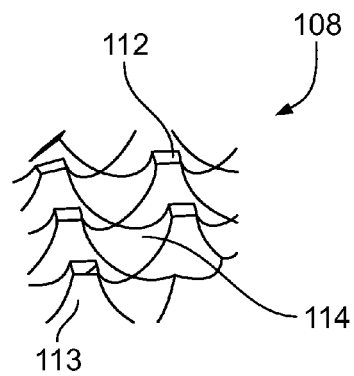
FIG. 15 is a top close up perspective view of teeth utilized on the endplate facing surface of the spacer.

FIG. 15 illustrates teeth 108 which comprise a penetrating face 112 that is sufficiently narrow or pointed to penetrate the bone of the endplate, and positional faces 113 that upon penetration abut the bone and prevent migration across the endplate. In this embodiment, the penetrating faces 112 have a small square footprint and the positional faces 113 have a sloped rounded pyramid profile. Positional faces 113 of teeth 108 broaden as they move away from the penetrating face 112 therein increasing anti-migration strength as spacer 100 settles into the endplate. A valley face 114 seats against the bone as a limit to subsidence of the spacer 100 into the bone. Teeth 108 in this embodiment are manufactured using a rounded cutter spaced 90 degrees apart.

Figure 9:
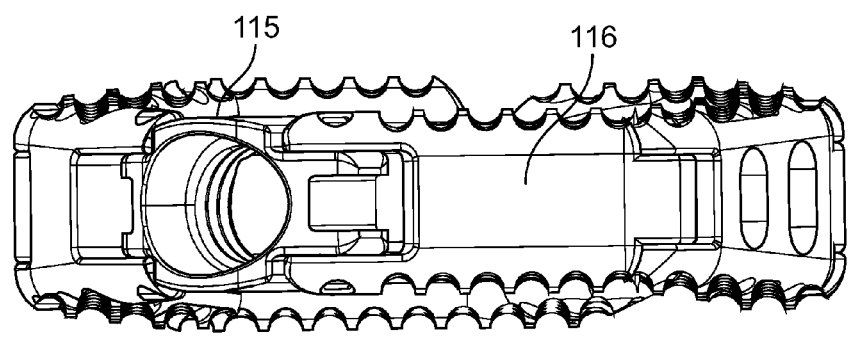
FIG. 9 is a posterior view of an expandable spacer adjusted for lordotic angle illustrating a decreasing height from anterior to posterior.

Leading the distal end 103 of spacer 100 is nose 109. The nose is configured for eased entry into the intervertebral space and may include tapered 110 and/or rounded 111 surfaces to ease the spacer 100 between the vertebral bodies and by pass soft tissue during entry. In the insertion configuration, spacer 100 assumes a narrow, compact, elongated form in order to minimize the size of the incision required for entry into the intervertebral space. From a lead end view (FIG. 6), the spacer 100 in this embodiment has a generally rectangular profile with support faces 106, 107 longer in length than the lateral 104 and medial 105 sides. In some embodiments, the support faces 106, 107 are sloped to fit a predetermined lumbar angle between the patient's vertebrae as can be seen in FIG. 9 wherein the anterior links of spacer 100 slope to greater heights moving towards the posterior links.

Figure 8A:
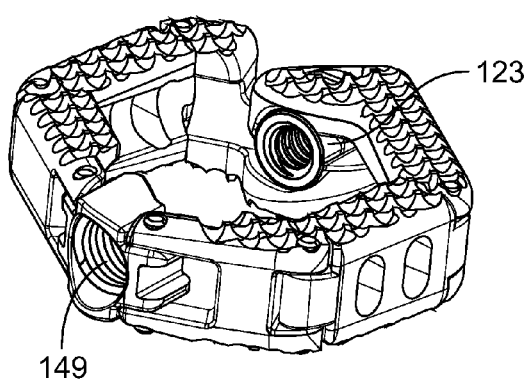
FIG. 8A is a proximal end perspective view of the bottom of an exemplary embodiment of an expandable spacer in its implanted configuration.
Figure 8B:
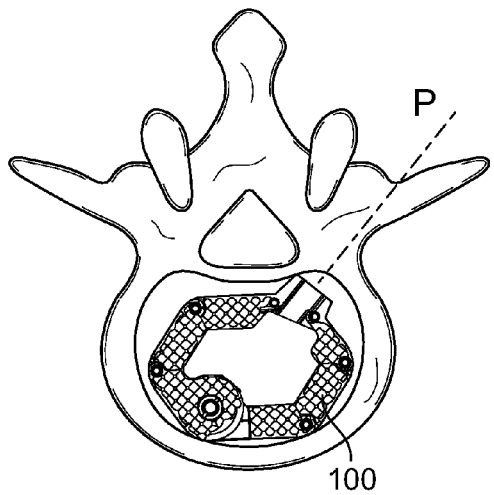
FIG. 8B is a superior view illustrating an expanded spacer resting on a vertebral endplate.
Figure 10:
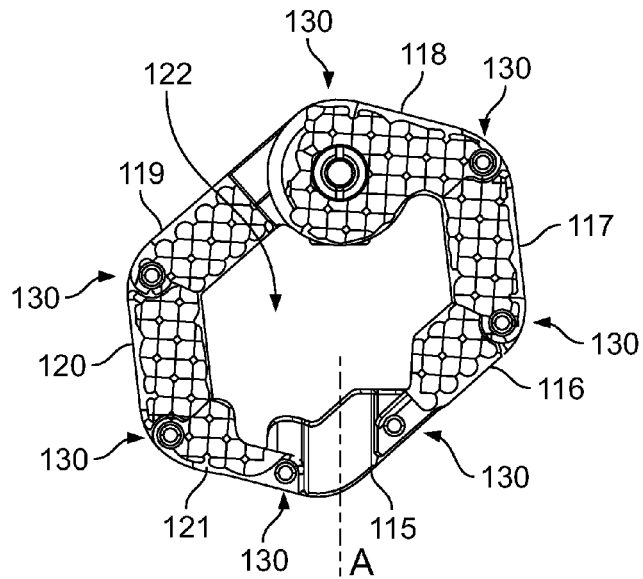
FIG. 10 is a top view of the implant illustrated in FIG. 8.

The vertebral body is strongest near the periphery of the endplate while the endplate profile is often described as oval, lima bean, or 'race track' shaped. Better fusions and overall better results are achieved when the interbody spacer is configured to rest on this dense bone near the endplate periphery while providing a large central graft aperture for the packing of bone graft. Therefore, in its expanded configuration, it is preferred that the outer perimeter of spacer 100 approximate the profile of the vertebral endplate as illustrated in FIG. 8A. Spacer 100 is illustrated in its expanded configuration in FIGS. 8-10. In this preferred embodiment, the spacer comprises seven links and forms an irregular hexagon to generally assume the outer endplate 'racetrack' profile. In other embodiments, the number of links utilized in the spacer may vary.

Figure 11:
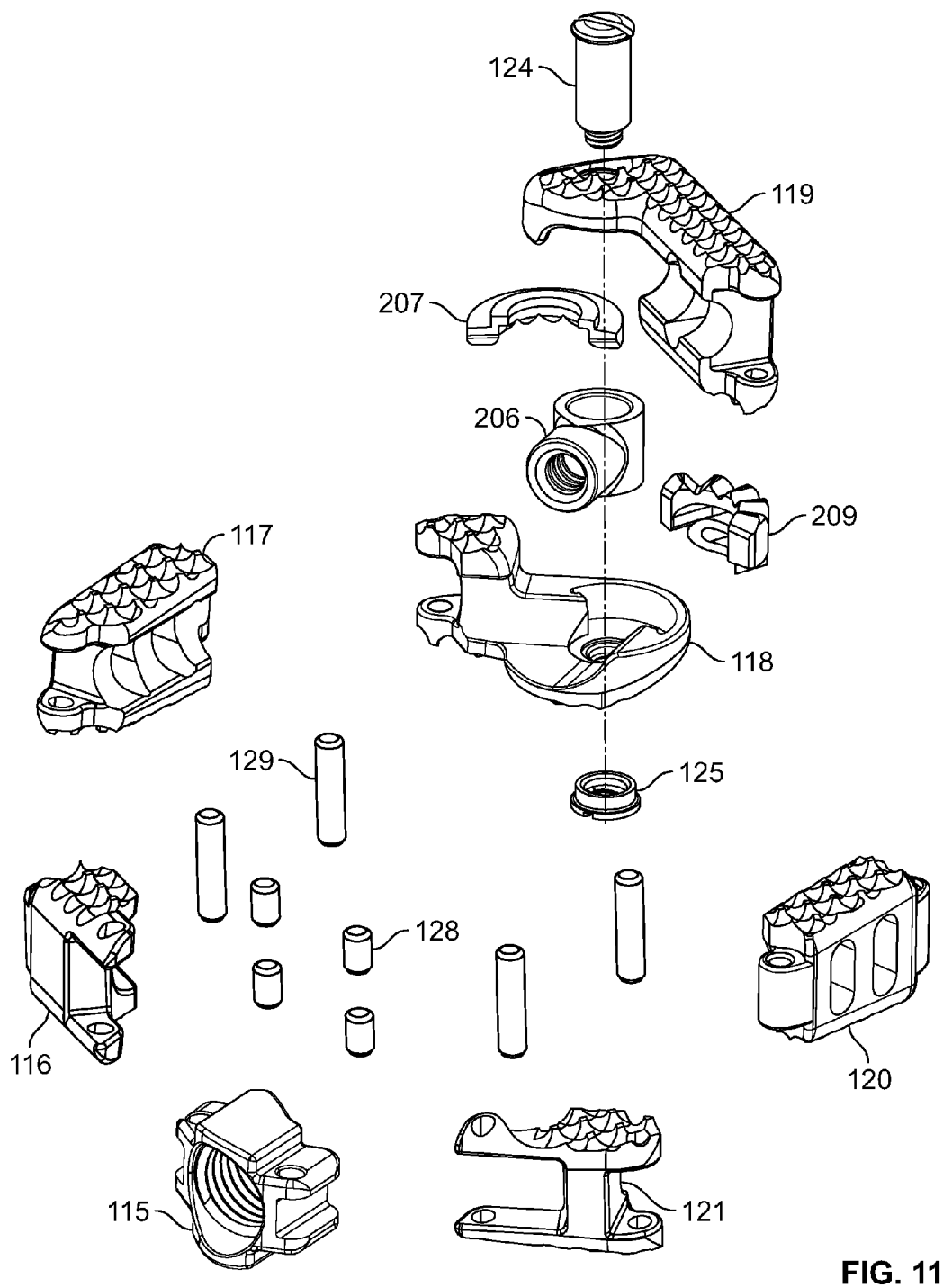
FIG. 11 is an exploded perspective view of the implant illustrated in FIG. 8.

FIG. 11 illustrates an exploded view of spacer 100 which is comprised of a plurality of links joined by joints 130. The links comprise insertion link 115 with central axis 'A' located at proximal end 102 of spacer 100 which serves as the site of attachment for inserter 300. Central axis 'A' is configured to be generally collinear with the surgical access path. For example, if spacer 100 was configured for a lateral surgical approach, insertion link 115 would preferably be placed lateral with central axis 'A' directed along a lateral direction. In this preferred embodiment, spacer 100 is configured for surgical insertion into the intervertebral space along a transforaminal surgical path indicated as 'P' in FIG. 8B. Insertion link 115 is therefore positioned posterior laterally and axis-A is directed in a posterior lateral direction. The spacer 100 in this embodiment is configured for use from either the left or right side of the spine wherein a support face 140 or 141 that faces superior when inserted from one side will face inferior when inserted from the other. Consistent with the transforaminal surgical approach, spacer 100 is inserted with a definitive medial and lateral side therein assuring alignment of the inserter link with the surgical path regardless of left or right side entry.

Joints 130 provide movement between each link portion 115-121 in a plane generally parallel to the intervertebral space. The joints may assume any variety of forms such as ball and socket, snap, hinge, or a pin or knuckle joint. Pin joints are utilized in the preferred embodiment and each link portion 115-121 comprises one or more capture tongue 158 configured to reside within a complementary capture groove 157 (FIG. 31,33) on an adjacent link portion 115-121 to form an endless chain. In the expanded configuration, this chain of links defines a graft aperture 122 available for packing with bone graft or other bone substitute.

Figure 28:
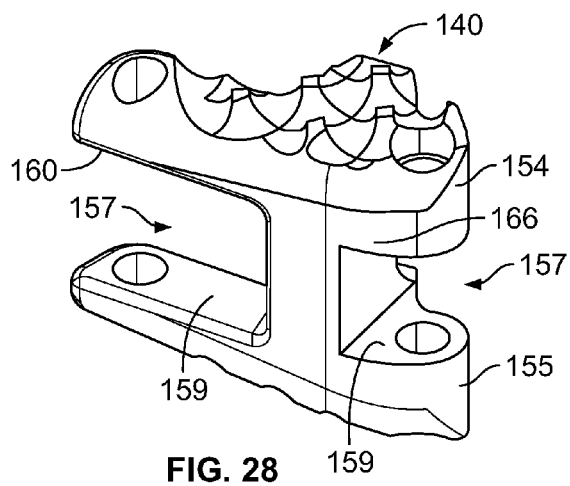
FIG. 28 is a front perspective view of an exemplary embodiment of a lateral proximal link of the implant.

Each link portion 115-121 of spacer 100 may share a plurality of common features not necessarily labeled on each link. For example, each link is formed from a body 167, each link except for the inserter link has teeth 108, and link support faces 140, 141 are common to each link and abut the endplates therein maintaining the predetermined intervertebral space. Adjacent links 115-121 comprise a capture groove 157 and a capture tongue 158 aligned within said groove to form a joint 130. Two capture walls 154 & 155 define capture groove 157. The interior of capture groove 157 comprises one or more capture surfaces 159-160 (FIG. 28,30). Capture tongue 158 (FIG. 34) comprises opposing guide surfaces 161 and 162. Pin wall 163 extends vertical through capture tongue 158 and capture walls 154 & 155 therein defining pin aperture 164 with central axis-B.

Figure 26:
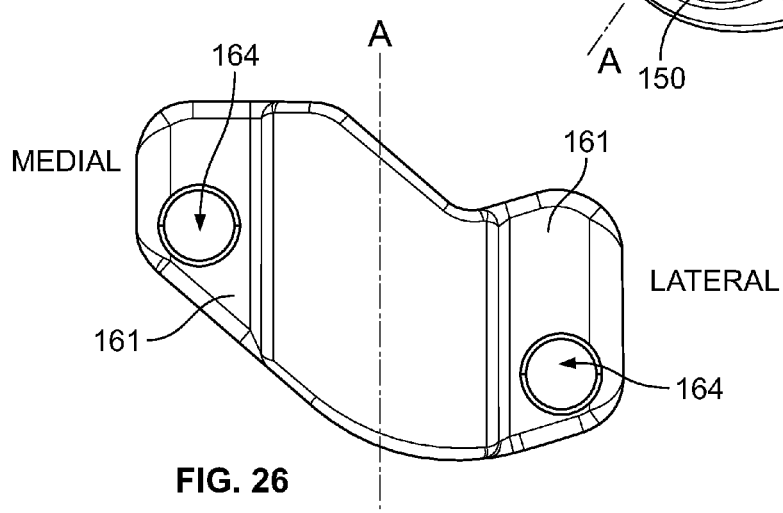
FIG. 26 is a top view of the inserter link of FIG. 25.

Joints 130 are formed by configuring a capture tongue 158 within capture groove 157 and aligning axis-B. Pivot pins 129 are then pressed into pin apertures 164 except with insertion link 115 wherein shortened pivot pins 128 are utilized within pin apertures 164 (FIG. 26). Each link 115-121 in this embodiment is configured with a predetermined profile suitable to performing in the insertion configuration, the expanded configuration, and transitional configurations therebetween. For example, FIG. 26 illustrates a generally S-shaped profile of the insertion link 115 from a top view.

At each joint 130, a plurality of positional stops 165 interfering with each other are configured to limit motion at each joint when spacer 100 moves from an insertion configuration to an expanded configuration. These positional stops 165 determine the final shape of the expanded implant. In the preferred embodiment for example, the positional stops 165 help guide the implant into the open generally hexagonal profile of FIG. 10.

Figure 25:
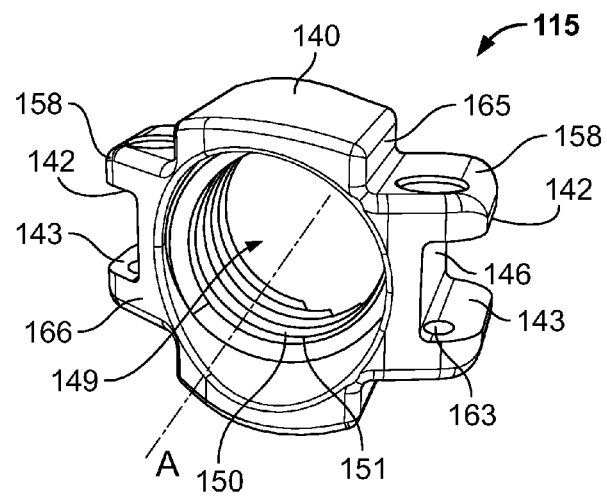
FIG. 25 is a proximal perspective view of an exemplary embodiment of an insertion link.
Figure 27:
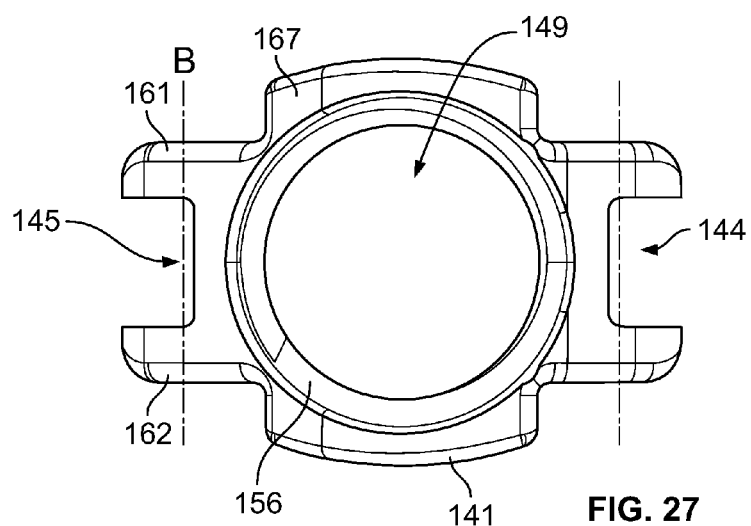
FIG. 27 is a proximal view of the inserter link of FIG. 25.

The insertion link 115, FIGS. 25-27, comprises a pair of opposing capture tongues 158. A control guide 144 is situated on insertion link 115 and in this embodiment is in the form of a pair of opposing grooves 145 cut parallel to axis-A through each control tongue 158. The grooves are configured to accept control arms 350 of inserter instrument 300 when mounted to insertion link 115. The grooves 145 comprise surfaces 146, 143, and 142 upon which surfaces on control arms 350 act to impart forces and direction on the insertion link 115.

An inner wall 151 extending along axis-A defines inserter aperture 149. Inner wall 151 may be threaded 150 for threaded attachment of insertion instrument 300. At the proximal end of insertion link 115 is instrument stop surface 156 which abuts instrument 300 when attached to insertion link 115.

Figure 29:
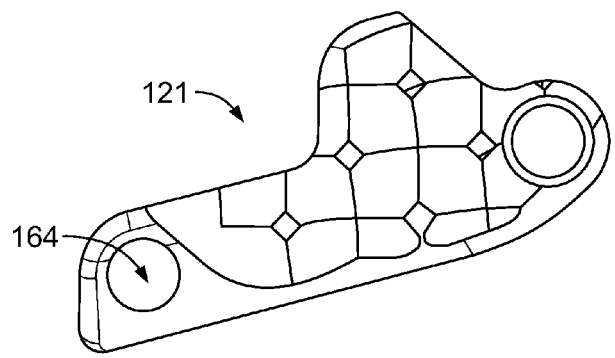
FIG. 29 is a top view of the link of FIG. 28.
Figure 30:
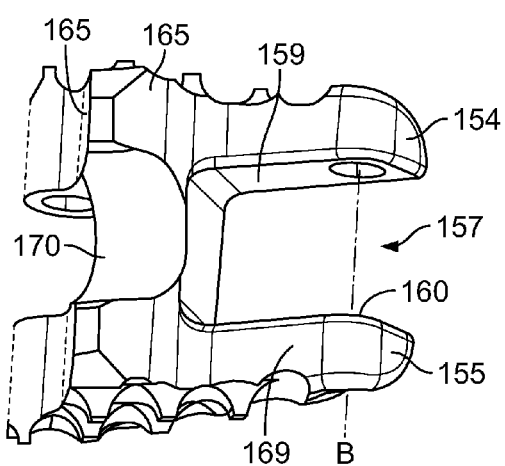
FIG. 30 is a rear perspective view of the link of FIG. 28.

The lateral-proximal (LP) link 121 is illustrated in FIGS. 28-30. This link is connected by pin joint to the lateral side of inserter link 151. LP link 168 comprises two capture grooves 157. The deeper capture groove 157 is configured to house the elongated capture tongue 158 of insertion link 115 when elongated wall 169 of LP link abuts positional stop 165 in the insertion configuration. Situated on the inside of link 168 is instrument channel 170. This channel accommodates portions of instrument 300 when spacer 100 is in the collapsed insertion configuration.

Figure 31:
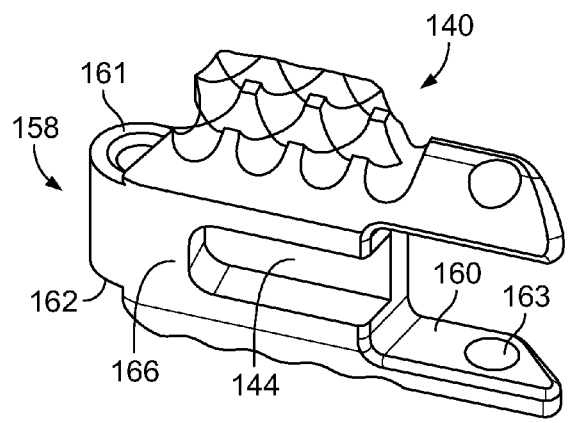
FIG. 31 is a front perspective view of a medial proximal link of the implant.
Figure 32:
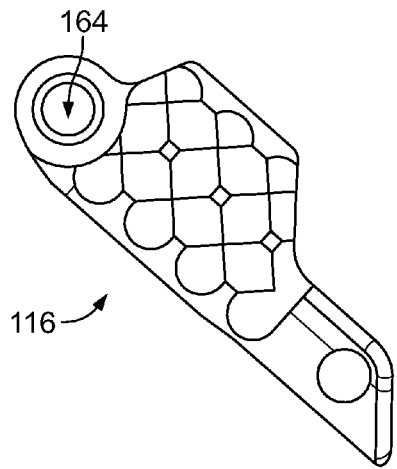
FIG. 32 is a top perspective view of the implant illustrated in FIG. 31.
Figure 33:
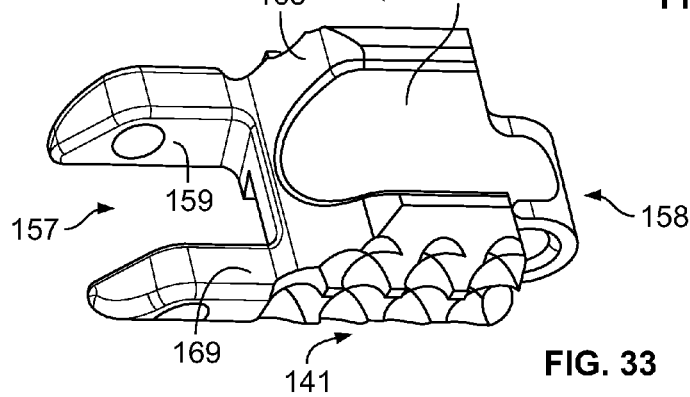
FIG. 33 is a rear perspective view of the implant illustrated in FIG. 31.

FIGS. 31-33 illustrate an embodiment of a medial proximal (MP) link Unlike LP link 121, the MP link 116 comprises both a capture groove 157 and a capture tongue 158. Some embodiments of the MP or LP links include an extension of control guide 144 in the outer surface of the link to accommodate control arms 350 of inserter instrument 300.

Figure 34:
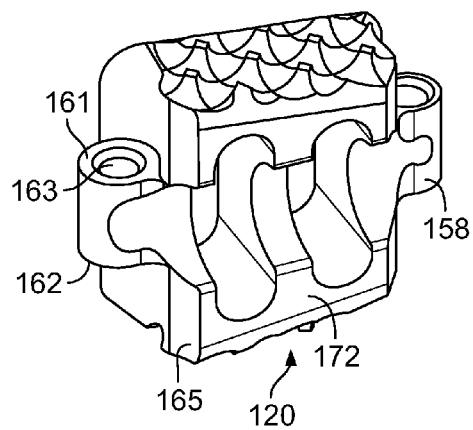
FIG. 34 is an inside perspective view of a lateral intermediate link of the implant.
Figure 37:
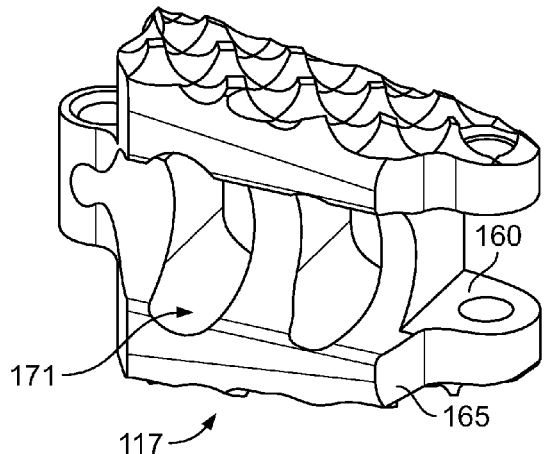
FIG. 37 is an inside perspective view of an exemplary embodiment of a medial intermediate link of the implant.
Figure 35:
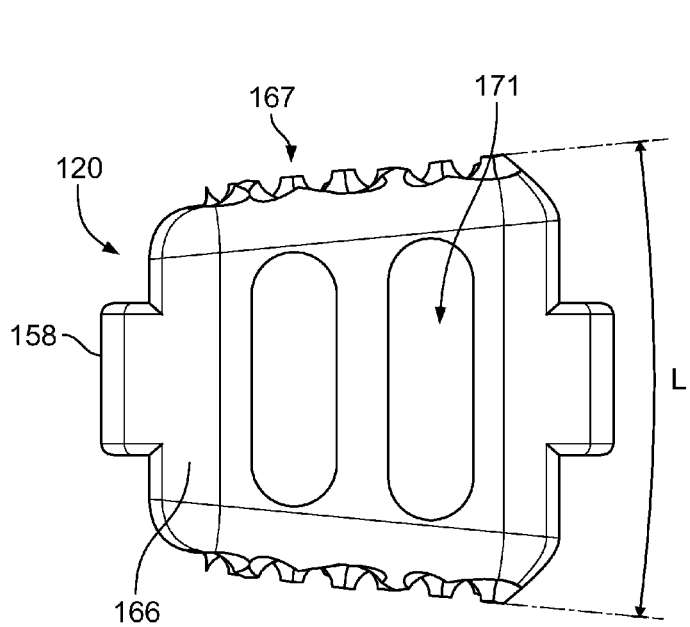
FIG. 35 is an outside view of the link illustrated in FIG. 34 and illustrating lumbar angle L.
Figure 36:
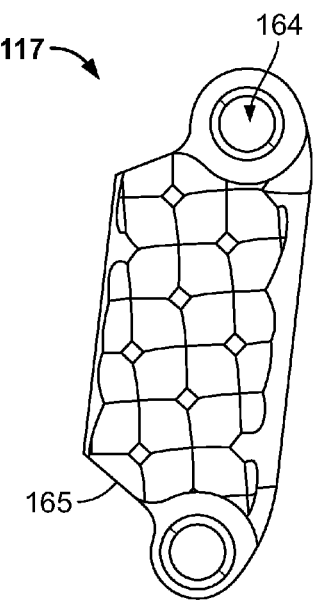
FIG. 36 is a top view of the link illustrated in FIG. 34.
Figure 38:
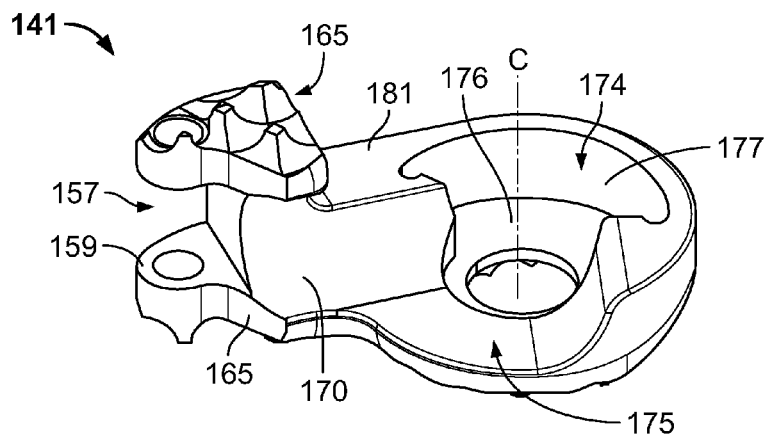
FIG. 38 is an inside perspective view of an exemplary embodiment of a medial distal link of the implant.
Figure 39:
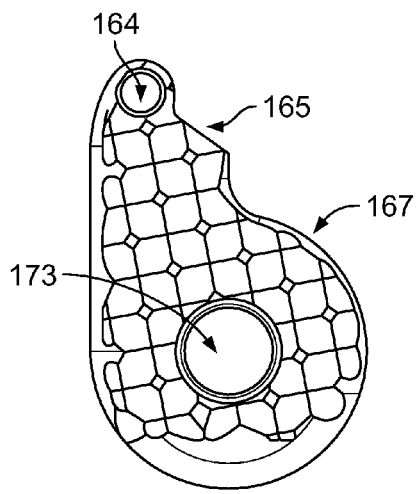
FIG. 39 is a bottom view of the medial distal link illustrated in FIG. 38.
Figure 40:
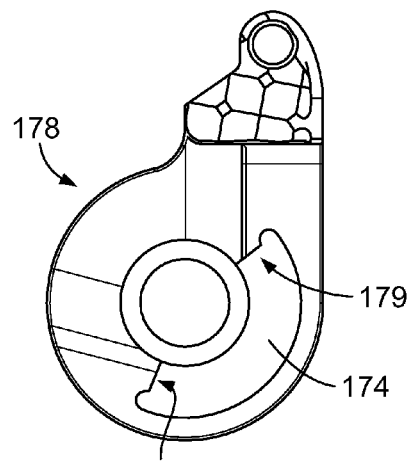
FIG. 40 is a top view of the medial distal link illustrated in FIG. 38.
Figure 41:
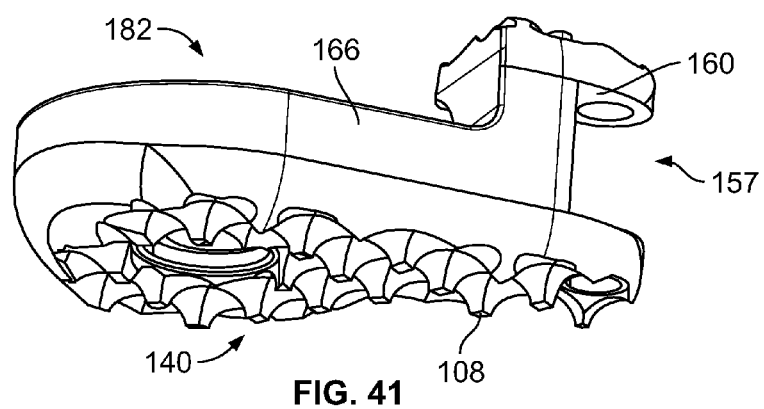
FIG. 41 is an outside perspective view of the medial distal link illustrated in FIG. 38.
Figure 42:
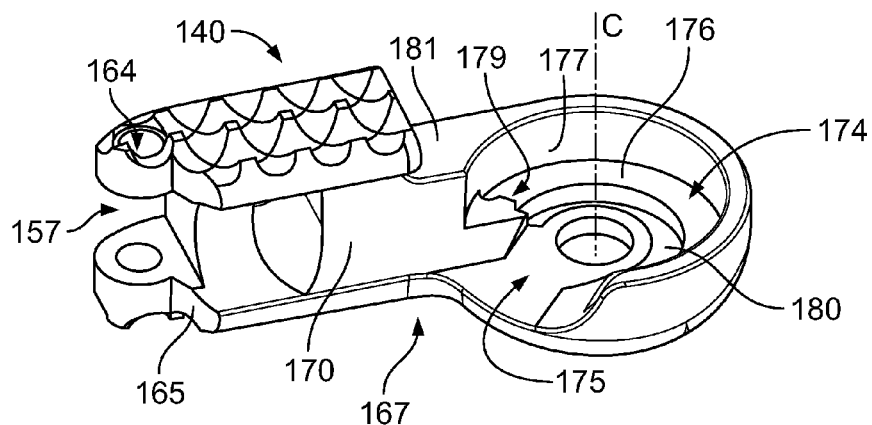
FIG. 42 is an inside perspective view of an exemplary embodiment of a lateral distal link of the implant.
Figure 43:
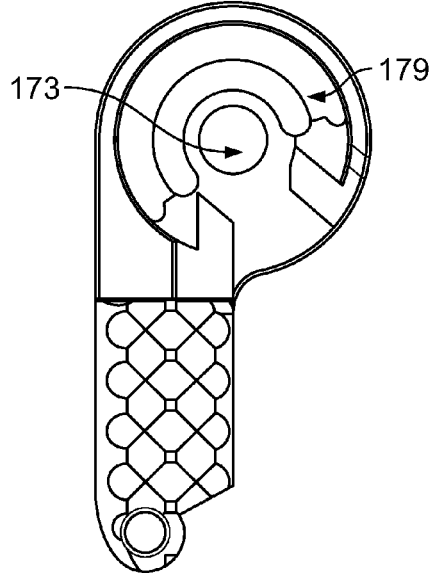
FIG. 43 is a top view of the lateral distal link illustrated in FIG. 42.
Figure 44:
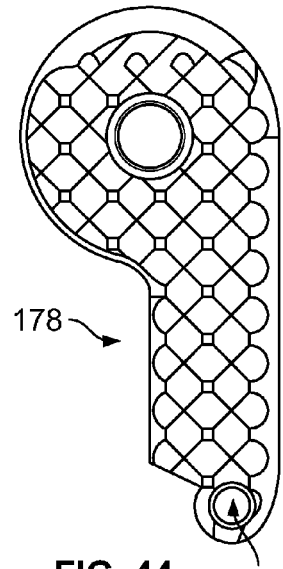
FIG. 44 is a bottom view of the lateral distal link illustrated in FIG. 42.
Figure 45:
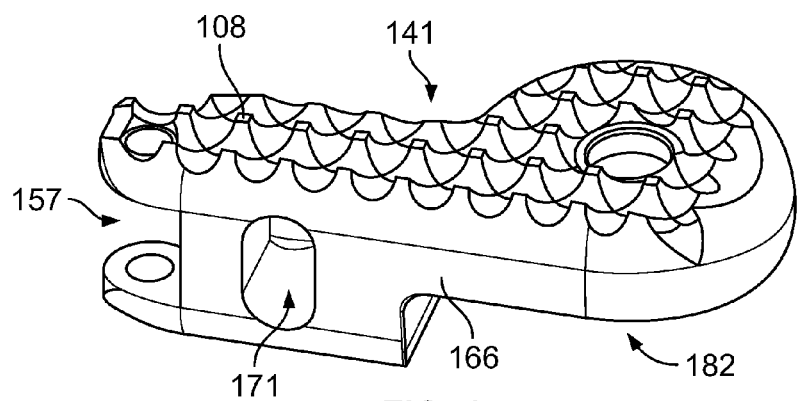
FIG. 45 is an outside perspective view of the lateral distal link illustrated in FIG. 42.
Figure 46:
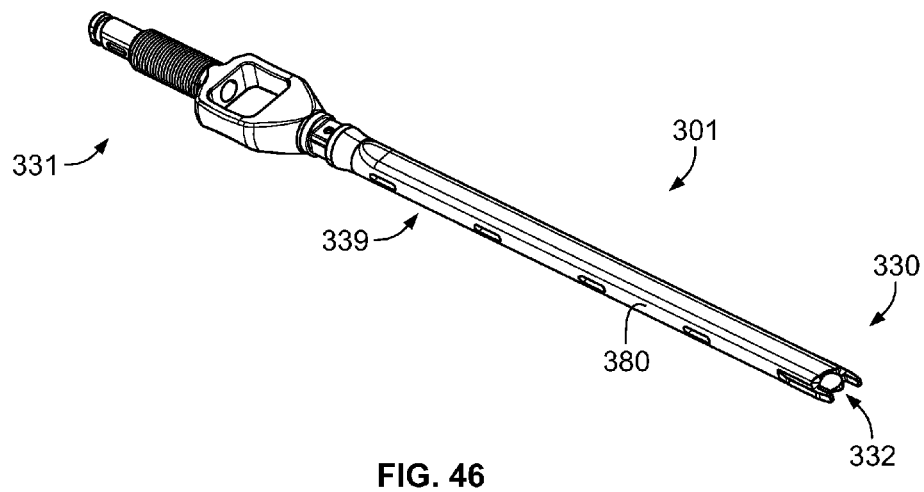
FIG. 46 is a front perspective view of an exemplary embodiment of the inserter's control frame.
Figure 47:
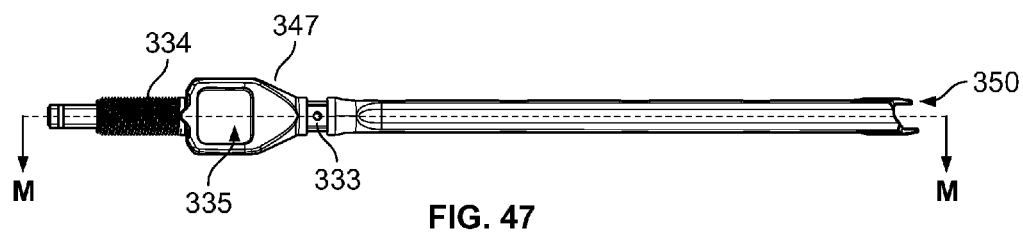
FIG. 47 is a top view of the control frame illustrated in FIG. 46.
Figure 48:
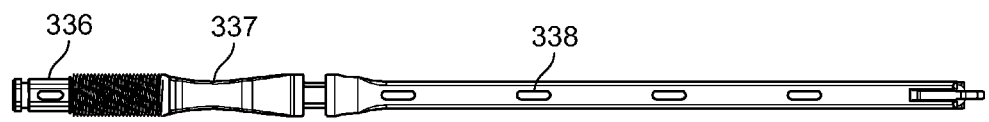
FIG. 48 is a side view of the control frame illustrated in FIG. 46.
Figure 49:
FIG. 49 is a cross-sectional view of the control frame illustrated in FIG. 46 along axis M-M.
Figure 50:
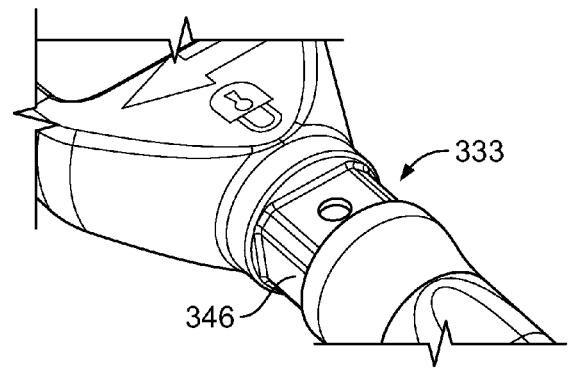
FIG. 50 is a top perspective close-up view of the neck portion of the control frame.
Figure 51:
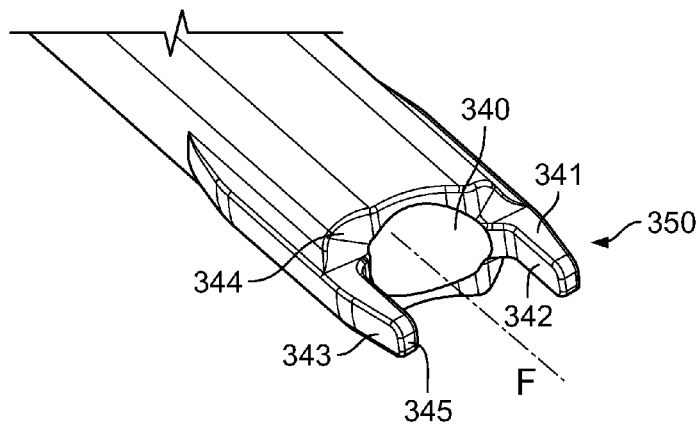
FIG. 51 is a distal end close up view of the control arms of the control frame.
Figure 52:
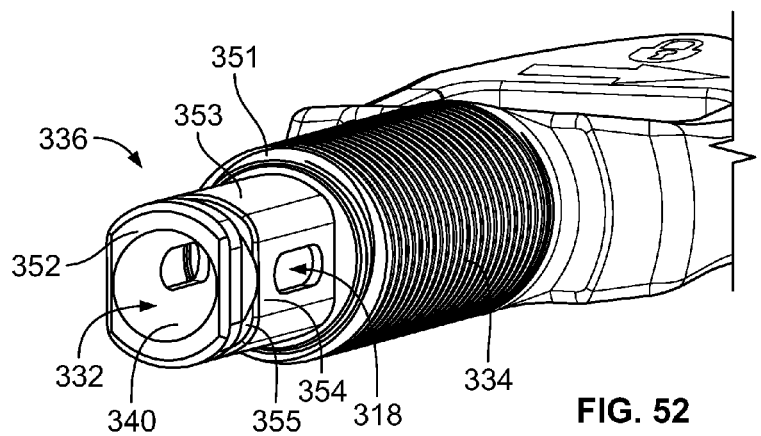
FIG. 52 is a proximal end close up view of the expansion limiter mount.

Various embodiments of the lateral intermediate (LI) link 120 is illustrated in FIGS. 34 & 35, and of the medial intermediate link (MI) 117 in FIGS. 36 & 37. The embodiments shown illustrate an angulation between support face 140 and 141 to replicate the lumbar angle 'L' typically encountered between the endplates. This angulation between support faces may be adjusted on any of the spacer links according to the anticipated final position within the intervertebral space. For example, if a link resides obliquely within the intervertebral space, then support faces may be angled accordingly to match the intervertebral space at this orientation.

LI link 120 utilizes a capture tongue 158 on each side of the link whereas the MI link 117 utilizes one capture tongue 158 and one capture groove 157. One or more windows 171 may be cut through the body 167 of link 117,120 between the inner 172 and outer 166 surface of the link.

FIGS. 38-41 illustrate various aspects of an exemplary embodiment of medial distal (MD) link 118 of spacer 100. Like the other links, the MD link comprises a body 167 formed in the general shape of the number six. At one end, is a capture groove 157 utilized for creating a joint with adjacent MI link 117. On one side of MD link 118 is an extensive support face 140 with teeth 108 inscribed thereon. On an opposing side is a smaller support face 141. Located centrally within the base of the 'six', is coupling aperture 173 sized to house shaft 201 of coupling screw assembly 200.

Situated between outer surface 166 and aperture 173 is positioner pocket 174. Pocket 174 is configured with a support floor 176, containing wall 177, and stop wall 179. Situated between inner surface 178 and aperture 173 is coupler window 175. Cut into body 167 is instrument channel 170 to accommodate portions of instrument 300 when spacer 100 is in its insertion configuration. The body 167 of MD link 118 and LD link include a mating cutaway 182 defining mating surface 181. MD link 118 and LD link 119 are aligned on axis-C with mating surface 181 of each link in facing opposition.

FIGS. 42-45 illustrate various aspects of an exemplary embodiment of lateral distal (LD) link 119 of spacer 100. Again, the LD link comprises a body 167 formed in the general shape of the number six. At one end, is a capture groove 157 utilized for creating a joint with adjacent LI link 120. One side of LD link 119 comprises an extensive support face 140 with teeth 108 inscribed thereon. On an opposing side is a smaller support face 141. Located centrally within the base of the 'six', is coupling aperture 173 sized to house shaft 201 of coupling screw assembly 200.

Situated between outer surface 166 and aperture 173 is positioner pocket 174. Pocket 174 is configured with a support floor 176, containing wall 177, and stop wall 179. Inscribed into support floor 176 is a C-shaped groove 180. Situated between inner surface 178 and aperture 173 is coupler window 175. Cut into body 167 is instrument channel 170 to accommodate portions of instrument 300 when spacer 100 is in its insertion configuration. The body 167 of MD link 118 and LD link 119 include a mating cutaway 182 defining mating surface 181. MD link 118 and LD link 119 are aligned on axis-C with mating surface 181 of each link in facing opposition.

Figure 12:
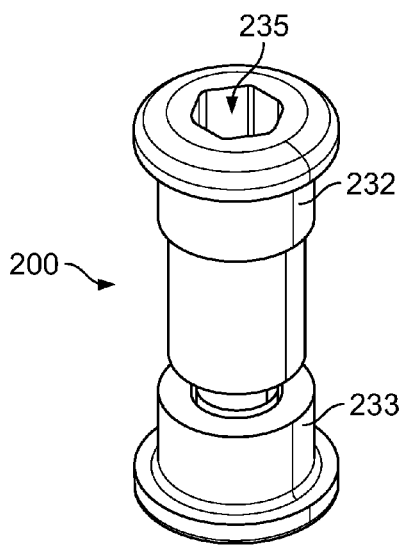
FIG. 12 is a front perspective view of an exemplary embodiment of a fastener pivot assembly.
Figure 13:
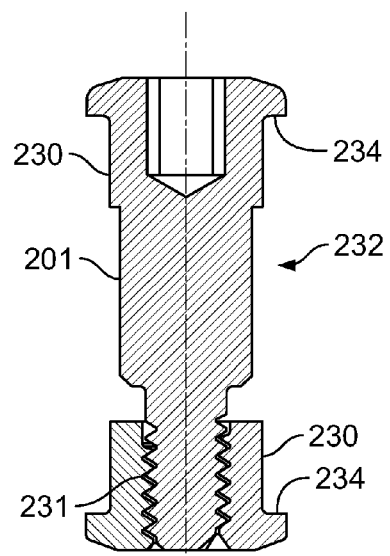
FIG. 13 is a cross-sectional view of the fastener pivot assembly illustrated in FIG. 12.
Figure 14:
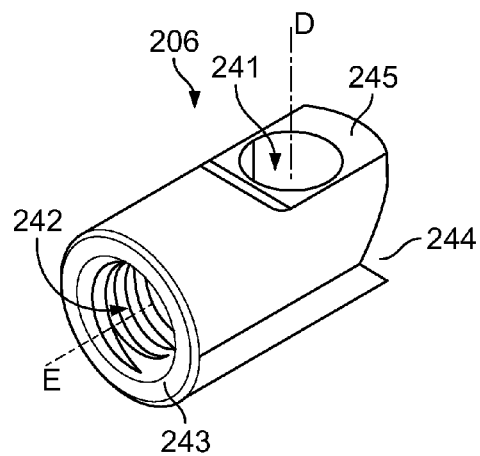
FIG. 14 is a front perspective view of an alternative coupling device.
Figure 16:
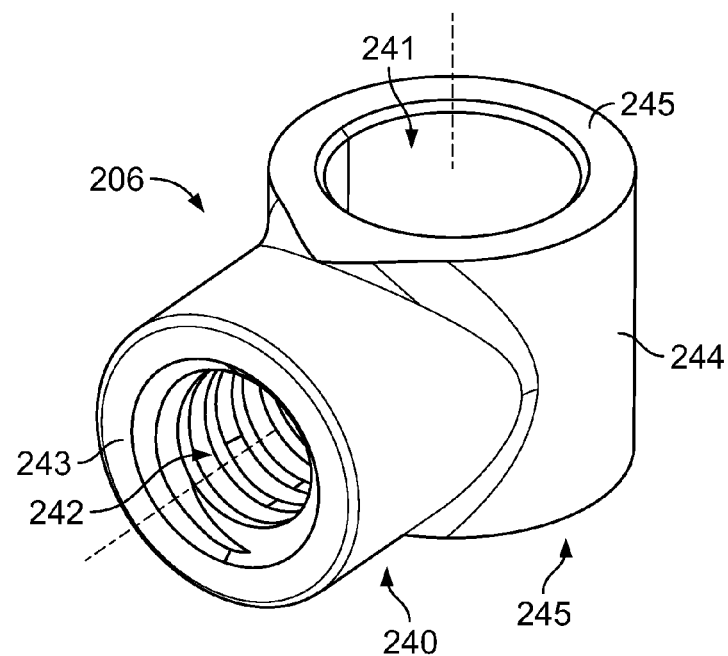
FIG. 16 is a front perspective view of an exemplary embodiment of a coupling device.
Figure 17:
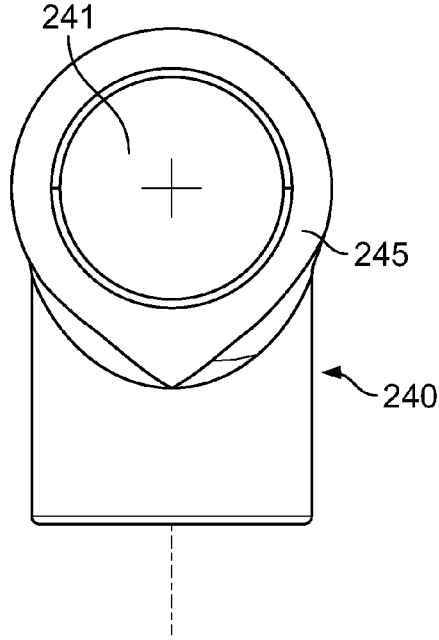
FIG. 17 is a top view of the coupling device illustrated in FIG. 16.
Figure 18:
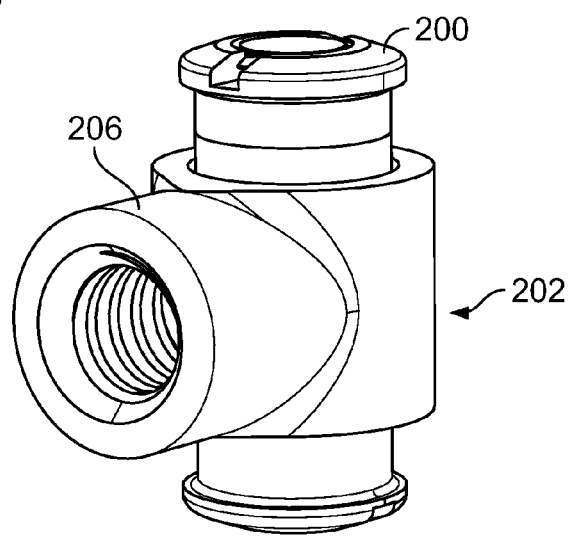
FIG. 18 is a front perspective view of an exemplary embodiment of a pivot coupler assembly.
Figure 22:
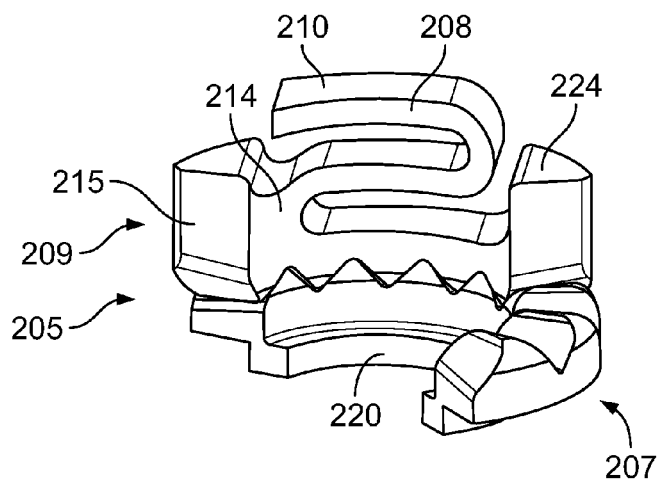
FIG. 22 is a front perspective view of an exemplary embodiment of a positioner gear assembly.
Figure 23:
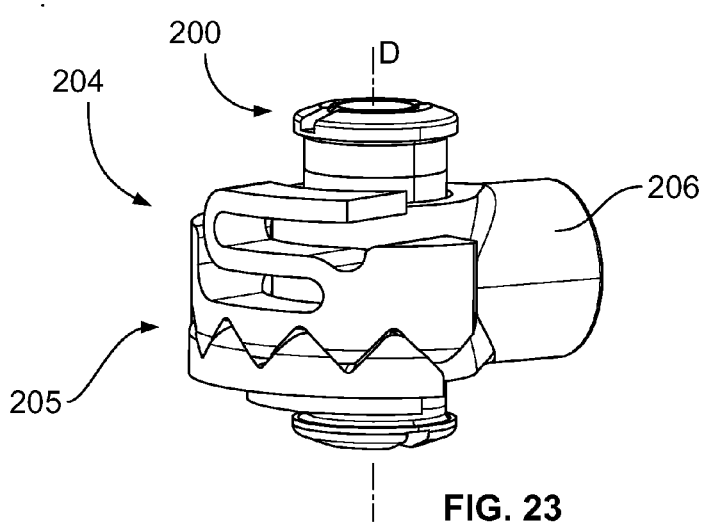
FIG. 23 is a rear perspective view of a positioner coupling assembly.

FIG. 23 illustrates positioner coupling assembly 204 which is comprised of; fastener pivot assembly 200 illustrated in FIGS. 12 and 13, positioner gear assembly 205 illustrated in FIG. 22, and coupler 206 illustrated in FIG. 16.

Fastener pivot assembly 200 secures MD link 118 and LD link 119 together and in this embodiment is in the form of a shoulder bolt 232 releasably attached to shoulder nut 233 through threaded interengagement 231. However, fastener pivot assembly 200 may be in other forms such as a rivet or a bolt threaded into the aperture of the opposing link Bolt 232 and nut 233 comprise opposing restraining faces 234 that secure links 118 and 119 together when nut 233 is advanced. The shoulders 230 on nut 233 and bolt 232 center links 118 and 119 along axis C. Coupler 206 comprises a rounded body 240 with pivot aperture 241 extending through body along axis D. A coupling aperture 242 extends along axis-E and is generally perpendicular to axis-D. The wall defining the coupling aperture 242 is threaded for engagement with expansion rod 304. Stop surface 243 abuts an opposing surface on expansion rod 304 indicating the rod is fully engaged in coupling aperture 242. Centering surface 244 encircles the outer body 240 about axis D. In an assembled configuration, end surfaces 245 position coupler 206 between the MD and LD links 118 & 119.

Figure 24:
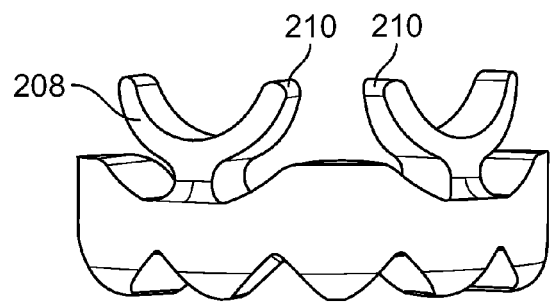
FIG. 24 is a rear perspective view of an alternative embodiment of a positioner gear with integrated spring.

Positioner gear assembly 205 is configured to hold spacer 100 in a predetermined expanded or collapsed configuration. Assembly 205 comprises an arc shaped integral spring positioner gear 209 mated with a complementing positioner gear 207 as illustrated in FIG. 22. Illustrated in FIG. 21, spring positioner gear 209 comprises a biasing element here in the form of an integrated undulating spring 208 or equivalent biasing member. Providing the space required to compress is compression gap 223 and limit face 224 abuts and stops further compression at support floor 176 to prevent plastic deformation of spring 208. A foot 210 of spring 208 resides against support floor 176 of MD link 118. In an alternate form, spring 208 may be in the form of a 'Y' as seen in FIG. 24 wherein the foot 210 is at the tip of arms of the Y, or other forms such a separate compression spring or leaf spring.

Figure 19:
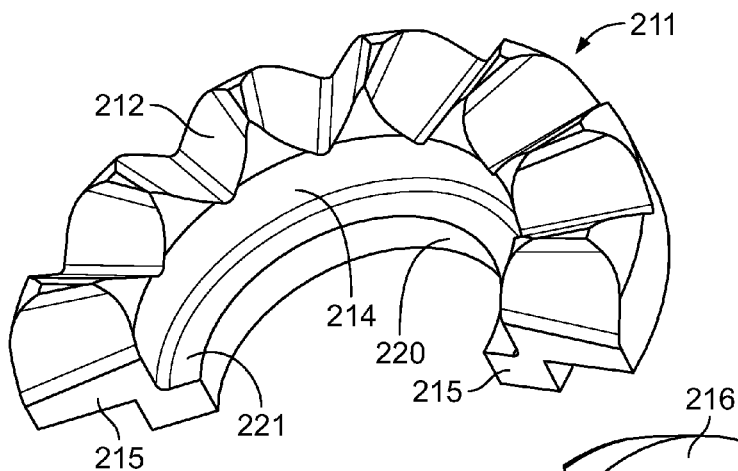
FIG. 19 is a top perspective view of an exemplary embodiment of a positioner gear.
Figure 20:
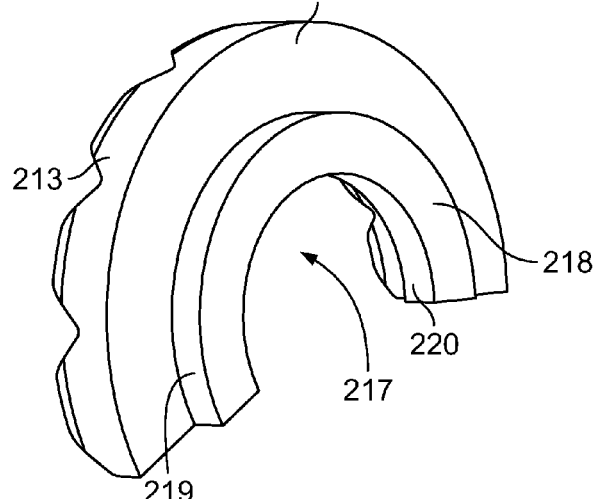
FIG. 20 is a bottom perspective view of the positioner gear illustrated in FIG. 19.
Figure 21:
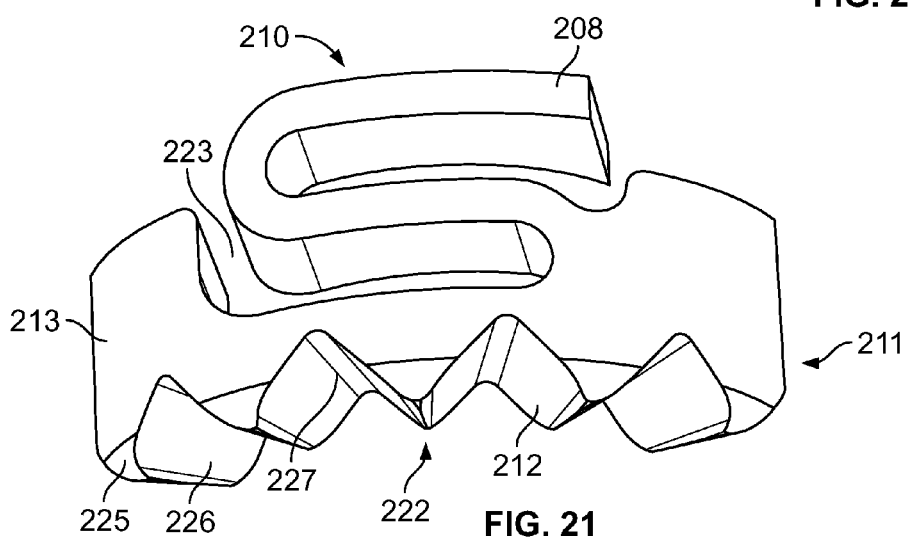
FIG. 21 is a rear perspective view of an exemplary embodiment of a positioner gear with integrated spring.

The positioner gears 209 and 207 comprise an arc shaped body 211 with radially cut teeth 212 cut into face wall 222. A convex outer wall 213 opposes a concave inner wall 214 sized to fit around centering surface 244 of coupler 206. At the ends of each arc are position faces 215. As illustrated in FIG. 19-21, positioner gear 207 comprises a seat face 216 opposite teeth 212. Stepping below the seat face 216 is inner rim 217 comprising an outer position face 219, an inner position face 220, bottom face 218, and top face 221.

In an assembled configuration, inner rim 217 of positioner gear 207 resides in C-shaped groove 180 of LD link 119 with seat face 216 directly adjacent support floor 176. End surface 245 of coupler 206 abuts against top face 221 to keep positioner gear 207 captured in positioner pocket 174. Position faces 215 of positioner gears are bound by stop walls 179 therein causing positioner gear 207 or 209 to rotate about axis C only as part of rotational movement of MD and LD links 118 and 119. Axis-E and coupling aperture 242 of coupler 206 reside within the coupler windows 175 of the MD and LD links with room to pivotably adjust as spacer 100 moves from an insertion configuration to an expanded configuration.

To create transition from insertion to expanded configuration, instrument 300 creates a tension force on coupler 206 drawing it near insertion link 115. During this motion, MD link 118 with captured spring positioner gear 209 housed within positioner pocket 174 and LD link 119 with positioner gear 207 captured within its own positioner pocket 174, rotate about axis-C in opposite directions. This rotational motion causes the opposing radial cut teeth 212 to move from a tip 225 to valley 227 orientation, to a tip 225 to tip 225 orientation therein imparting a translational motion of spring positioner gear 209 against spring 208. Continued rotation will cause tip 225 to seat in a new valley 227. This mechanical arrangement provides the surgeon a means to selectively expand or contract spacer 100 to predetermined positions once the instrument 300 imparts a sufficient tension or compression force on coupler 206. Similarly, spacer 100 will remain in the predetermined expanded configuration once instrument 300 is removed as the patient's anatomy will be unable under normal circumstances to create forces on spacer 100 sufficient to overcome biasing force of spring 208.

In an alternative embodiment, a nitinol leaf spring is configured about centering surface 244 of coupler with each leg of the leaf spring extending into the body of MD link 118 and LD link 119. Said spring biases link 118 and 119 towards an expanded configuration with inserter 300 configured to work against bias force to keep spacer 100 in insertion configuration during insertion.

The spacer inserter 300 and its components are now described in greater detail. The inserter 300 comprises a control frame 301 with proximal end 331 and distal end 330 and is illustrated in FIGS. 46-57. The frame 301 comprises an elongated body 339 with an interior wall 340 defining a central working aperture 332 sized for gliding passage of fixation tube 303 and expansion rod 304 (FIG. 2). The outer wall 380 extends from the distal end 330 with a rectangular profile similar to spacer 100 in the insertion configuration. Extending from the distal end 330 of body 339 are one or more control arms 350 sized to be received within the opposing grooves 145 of control guide 144 of insertion link 115. The control arms 350 comprise a plurality of torque walls 341 facing surfaces 142 and 143 on insertion link 115 and are configured to transmit a torsional force to the insertion link 115. Surfaces 146 of the inserter link are captured between opposing walls 342 therein aligning axis-A of inserter link with axis-F of control frame 301. Outer surfaces 343 of the control arms are sloped to minimize resistance against soft tissue during insertion and tip 345 is rounded for the same purpose. Link face 344 is secured against stop surface 156 when spacer 100 is attached to spacer inserter 300. In this embodiment, link face 344 and stop surface 156 comprise complementary non-planar surfaces assuring proper alignment of spacer and inserter (i.e. lateral side 104 of spacer and side marked 'lateral' on inserter 300 are co-aligned).

Proximal to control arms 350 are one or more windows 338 cut into body 339 to enhance cleaning after use. At an area along body 339 positioned to reside above the skin when spacer 100 is fully inserted is a counter-torque neck 333 for attachment of a counter torque instrument. The counter-torque neck 333 is in the form of a plurality opposing torque faces 346 wherein an instrument as simple as an open ended wrench may attach and limit torsional forces transmitted to the implant through inserter 300.

Also at proximal end 331 of control frame 301 is a bulb portion 347 of body 339. Cut into bulb portion 347 is lock aperture 335 configured to house lock wheel 348. Two sides of bulb 347 are substantially flattened into opposing finger faces 337 to provide access by the user's fingers to lock wheel 348. Proximal along axis-F of body 339 from bulb portion 347 is collar neck 334 comprising threads 349 thereon configured for engagement with handle collar 302. At the proximal end of threads 349 is indicator 351 here illustrated in the form of a groove. The groove may be painted or otherwise highlighted. Located proximal to collar neck 334 of body 339 is limiter neck 336. The limiter neck comprises a proximal wall 352, a centering wall 353, a locator wall 354, and a limiter groove 355. In some embodiments limiter neck 336 is absent.

Figure 53:
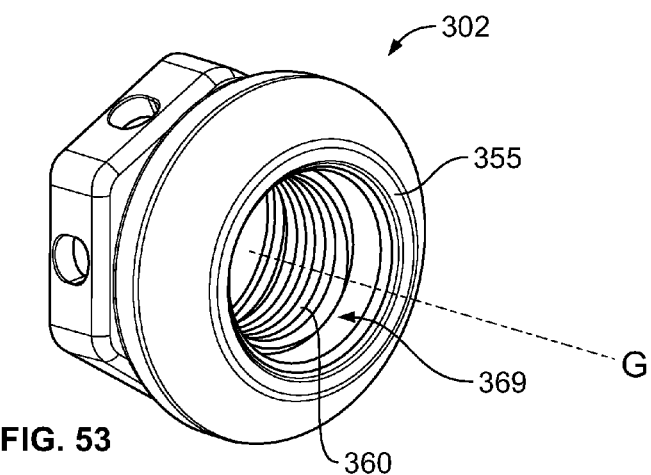
FIG. 53 is front perspective view of an exemplary embodiment of the handle collar assembly.
Figure 54:
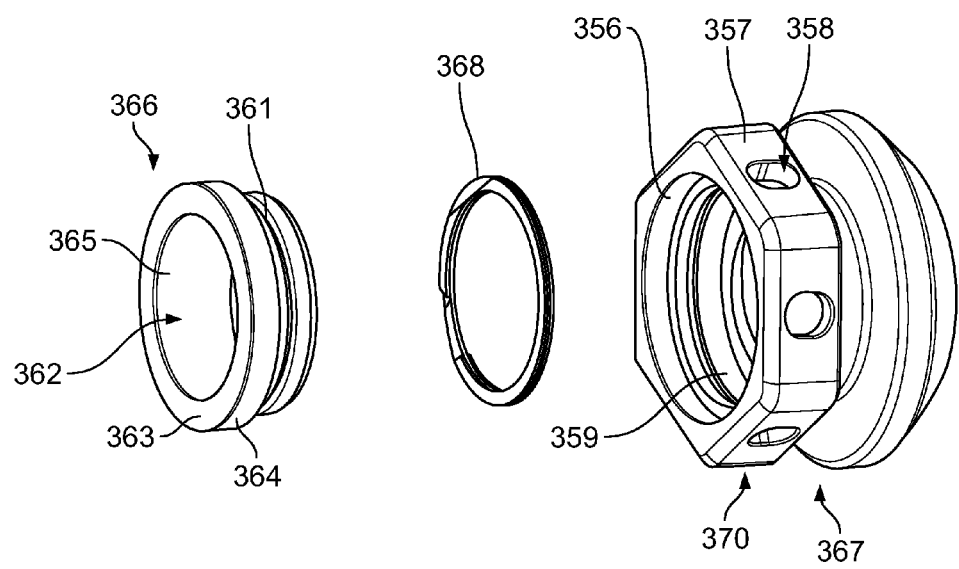
FIG. 54 is an exploded view of the handle collar assembly illustrated in FIG. 53.

Handle collar 302 assembly is illustrated in FIGS. 53 and 54 and comprises an outer drive collar 367 and inner spin collar 366. The outer drive collar 367 comprises a central aperture 369 with threaded walls 360 configured for threaded engagement over threads of collar neck 334. At the proximal end of outer drive collar 367, aperture 369 is enlarged to house inner spin collar 366. Within this enlargement is collar groove 359 for seating expansion ring 368. Ring 368 also encircles inner spin collar 366 within ring groove 361 therein securing inner spin collar 366 within outer drive collar 367 but providing for free rotation of one collar about the other.

Outer collar 367 also comprises a distal stop surface 355 which when abutted against bulb portion 347 is configured as the starting point for collar 367 prior to transitioning spacer 100 from insertion configuration to expanded configuration. Distally on outer collar 367 is drive 370 configured for moving collar by attachment of expansion handle 306. Drive 370 in this embodiment is in the form of several flat drive surfaces 357 formed in a hexagon encircling central aperture 369. Cut into each drive surface 357 is lock aperture 358. Proximal to inner threaded walls 360 is inner surface 356 sized to house outer surface 364 of inner spin collar 366. Inner spin collar 366 further comprises a spin aperture 362 defining an inner surface 365 enlarged to ride slightly above collar neck 334 threads. At proximal end of spin collar 366 is limiter surface 363.

Figure 55:
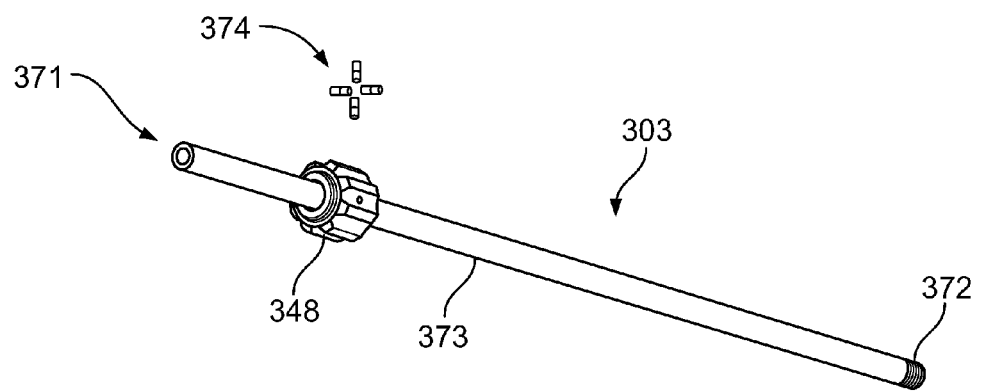
FIG. 55 is a front perspective view of an exemplary embodiment of a fixation tube with lockwheel and fixators.

Fixation tube 303 is further illustrated in FIG. 55. The tube 303 comprises a linear elongated body with inner cannula 371 extending the length of the tube and cannula sized to house fixation rod 304 to slide therein. The outer surface 373 of tube 303 at the distal end is configured with threads 372 for threaded engagement with threads 150 of insertion link 115. Nearing the proximal end, tube 303 is perforated with pin apertures. Fixators 374 in the form of fixation pins extend through lockwheel 348 and are housed within said pin apertures to fix lockwheel 348 in a predetermined location on tube 303 wherein when tube 303 is housed within control frame 301, lockwheel 348 freely spins within lock aperture 335.

FIGS. 2 and 4 further illustrates expansion rod 304. Protruding from the distal end of rod 304 is a threaded boss 375 configured for threaded engagement within coupling aperture 242. Stop surface 376 abuts stop surface 243 of coupler 206 when rod 304 is fully engaged within aperture 242. At step 320, rod 304 decreases in diameter.

The expansion limiter 305 prevents over expansion of spacer 100 when transitioning to the expanded configuration by limiting travel of expansion rod 304. The limiter 305 comprises a housing 315 with non-circular inner aperture 377 complementing profile of limiter neck 336 for sliding translational movement but not rotary. Cut into side of housing 315 is clip slot 378 configured for sliding entry of clip 318 therein securing housing 315 to expansion rod 304 proximal to step 320. Lock button 316 is housed in a button aperture 394 on side of housing (not viewable). Lock button 316 comprises elongated slot 317 wherein a rib (not viewable) within slot 317 releasably engages limiter groove 355 of control frame 301. Biasing member 379 keeps rib engaged in groove 355 until lock button 316 is depressed by user providing for release of limiter 305 from limiter neck 336.

Figure 56:
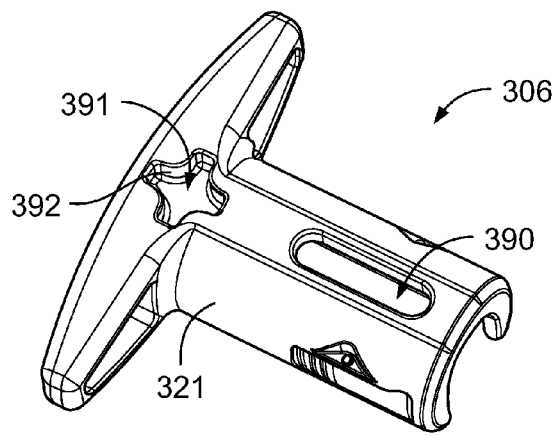
FIG. 56 is a rear perspective view of an exemplary embodiment of an expansion handle.
Figure 57:
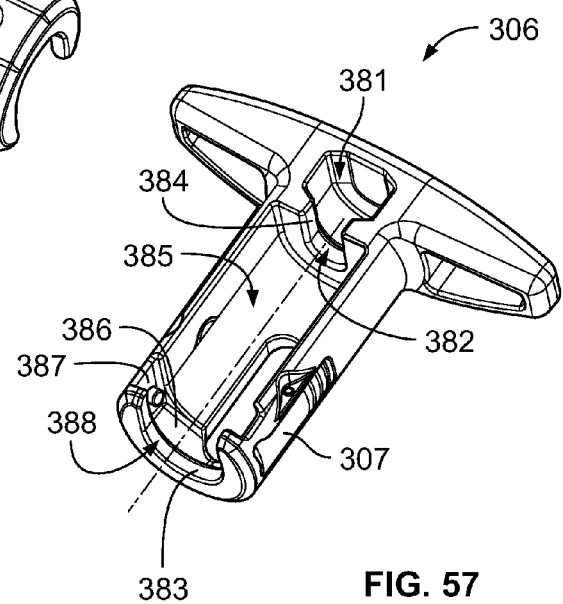
FIG. 57 is a front perspective view of the expansion handle illustrated in FIG. 56.

Expansion handle 306 comprises a T-shaped body 321 as illustrated in FIGS. 56-57 and FIG. 4. Cut into the front side of body 306 is head recess 381 sized to house enlarged head 310 of expansion rod 304. At the base of the head recess 381 is head shelf 384 to capture head 310 in head recess 381. Cut into head shelf 384 is a narrowed neck slot 382 to provide passage of the elongated rod body of expansion rod 304. Distal to head shelf 384 is limiter recess 385 configured to house expansion limiter 305. Collar recess 386 is situated distal to limiter recess 385, and is configured to fit over handle collar assembly 302. The collar recess 386 is bounded by two opposing collar drive surfaces 387 and a collar shelf 383. Cut through collar shelf 383 is control aperture 388 sized to pass collar neck 334 of control frame 301 while simultaneously capturing outer drive collar 367. This open configuration of head recess 381, neck slot 386, limiter recess 385, collar recess 386, and control aperture 388 provide the means for rapid sideways removal of expansion handle 306 from the inserter 300. With handle 306 connected to inserter 300, torsional force applied by user to handle is transmitted through collar drive surfaces 387 to drive surface 357 of outer drive collar 367 therein causing handle collar assembly 302 to advance proximal or distally along with expansion rod 304 further causing spacer to transition between insertion and expanded configuration.

One or more handle locks 307 releasably secure expansion handle 306 to handle collar 302. Each lock 307 comprises a lock lever 389 and bias member 312 in the form of a coiled spring. The lock lever 389 in this embodiment is in the shape of a teeter-totter comprising a pivot member 313 in the form of a pin, and a plunger 314. Lock lever 389 resides in lever recess 311 within body 321 of handle 306. The lever 389 is pinned into recess 311 by pivot member 313 extending between pivot apertures 309 and through body of lever 389. Spring force produced by bias member 312 causes plunger 314 to occupy plunger hole 310 and extend into collar recess 386 while simultaneously filling lock aperture 358 of outer drive collar. The handle is removed by the user by placing finger force on lever release surfaces 308 therein causing plungers 314 to retract and sliding handle 306 away.

On the rear side of expansion handle 306 is viewing window 390 cut between the outer wall of body 321 into limiter recess 385. Although expansion limiter 305 is viewable from the opposing side of the handle 306, window 390 provides a more intuitive method for viewing progress of spacer 100 transition from one configuration to another by noting position of limiter within window 390. For convenience, head drive pocket 391 is integral to expansion handle 306. This pocket 391 is configured with drive faces 392 complementing enlarged head 310 of expansion rod 304 wherein when handle 306 is removed from collar 302, it can be used to apply greater torque to head 310 when necessary.

Figure 58:
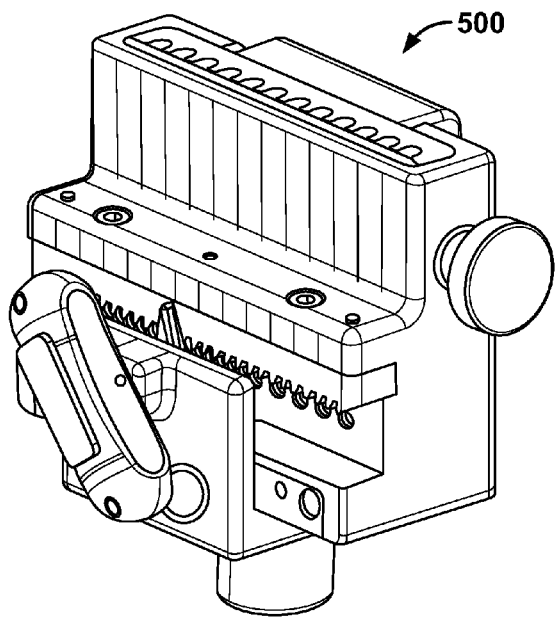
FIG. 58 is a front perspective view of an exemplary embodiment of a graft inserter assembly.

There are several different approaches to filling spacer 100 with graft material once inserted into the pre-determined location within the intervertebral space and transitioned to the expanded configuration. The insertion instrument may be removed and a graft filling instrument may be attached to insertion link 115. This instrument may be the form of an upright funnel with an elongated plunger at the proximal end, wherein the plunger pushes graft material down an elongated tube extending to the insertion link and into graft aperture 122. In an exemplary embodiment, a graft inserter assembly 500 is illustrated in FIG. 58. The graft inserter is configured to cooperate with the spacer & insertion assembly 101 to introduce bone graft into graft aperture 122 of spacer 100. The inserter 500 comprises a graft cartridge portion 501, a cartridge retainer portion 502, and a graft delivery guide portion 503.

Figure 66:
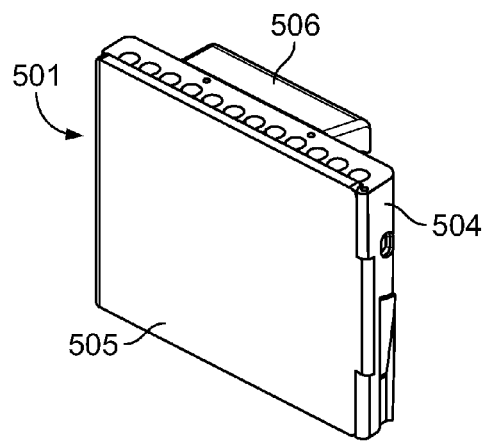
FIG. 66 is a front perspective view of a graft cartridge portion of graft inserter assembly of FIG. 58.
Figure 67:
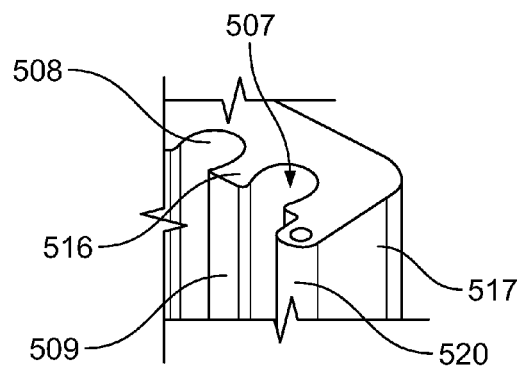
FIG. 67 is a front perspective closeup view of the chutes of the graft cartridge portion.
Figure 68:
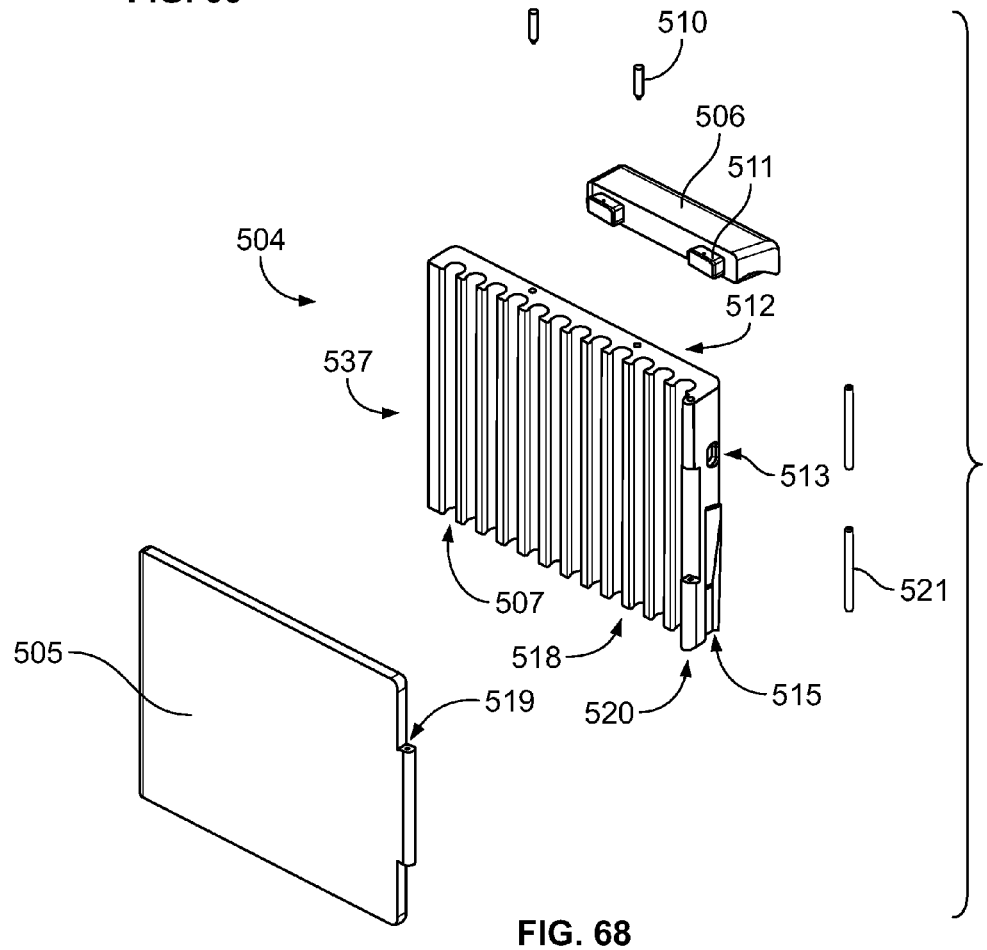
FIG. 68 is an exploded view of a graft cartridge portion.

The graft cartridge portion 501 in this embodiment is further illustrated in FIGS. 66-68. It comprises a chute housing 504, a cartridge door 505, and cartridge handle 506. The housing 504 is formed of a flat rectangular body 537 with a plurality of chutes 507, in this case partially opened, traveling from a proximal end top surface 516 to a distal end bottom surface 518 of chute housing 504. The chutes 507 have a chute wall 508 defining a cylindrical aperture configured for storage of graft and passage of a plunger to push the graft material in the chutes 507 from a proximal end to a distal end of the chute. The plunger for example, may be in the form of the expansion rod 304 described earlier but with a blunt tip and length sufficient to push bone graft from the chutes 507 into graft aperture 122 of spacer 100. The chutes 507 may be open on one side along their length and separated by chute divider surface 509.

A handle 506 is fixed to chute housing 504, here by means of fixing pins 510 holding posts 511 in bores 512 located on the opposing side of chute housing 504. Handle 506 provides eased insertion and removal of chute housing 504 from cartridge retainer portion 502. A lock recess 513 cooperates with a releasable lock 514, here in the form of a spring pin on the cartridge retainer 502 to secure chute housing 504 within retainer 502. A pair of opposed channels 515, one of them wedged, are situated within side wall 517. The channels 515 cooperate with bosses (not shown) within the cartridge retainer 502 to assure the chutes are properly centered within the retainer for the transfer of graft material therethrough.

A cartridge door 505, here in the shape of a flat square, comprises a hinge channel 519 for cooperation with hinge channel 520 and hinge pins 521. When removed from cartridge retainer portion 502, the graft cartridge 501 may be placed on a table laying on handle 506 with the graft door 505 opened therein exposing the open chutes 507. Graft is then spread across the chute divider surfaces 509 and massaged into the open chutes until they are full. Excess graft is wiped from surface 509 and the graft door 505 is closed. The graft cartridge 501 can then be inserted into the retainer portion 502.

Figure 59:
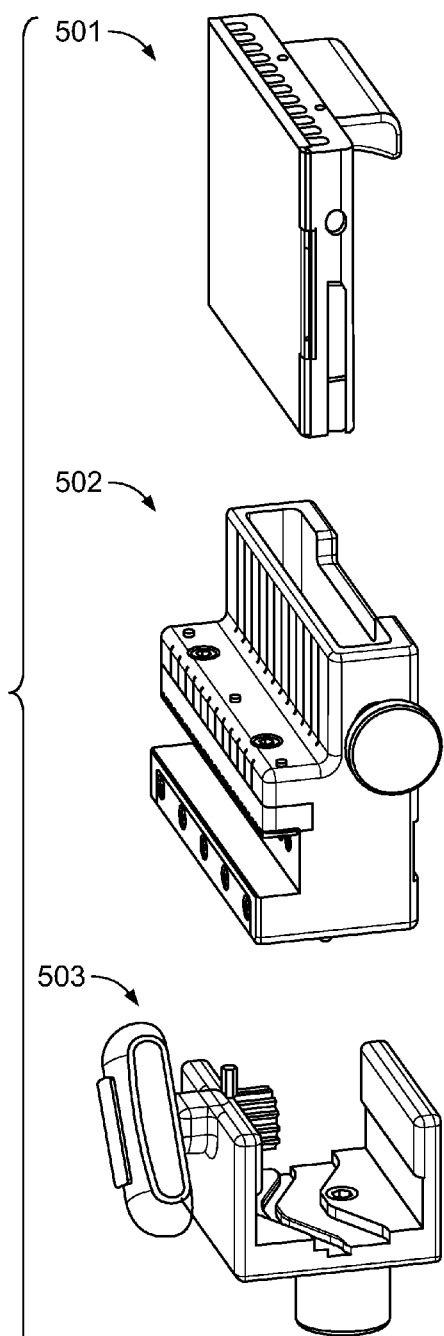
FIG. 59 is an exploded view of 3 components of the graft inserter assembly illustrated in FIG. 58.
Figure 60:
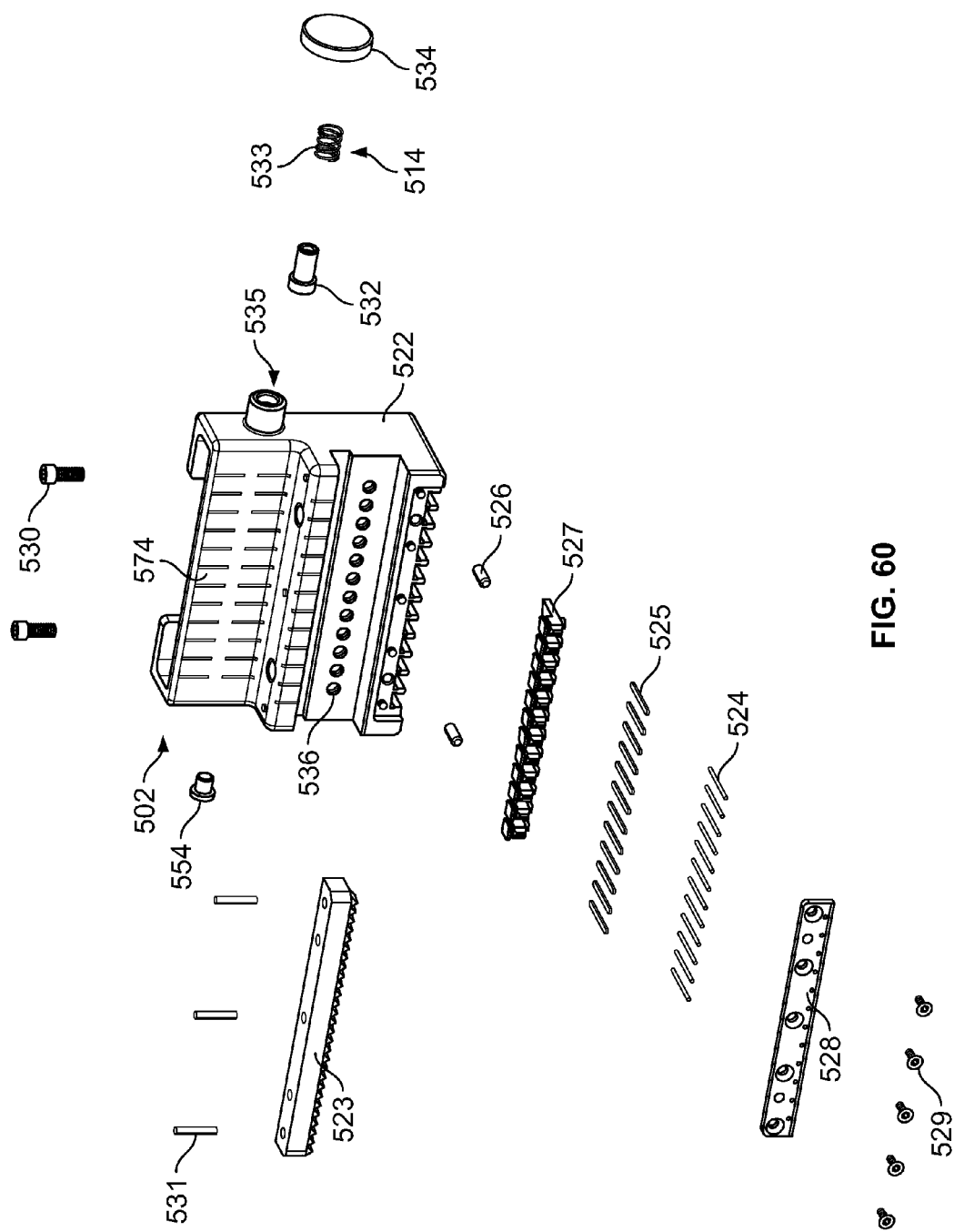
FIG. 60 is an exploded view of a cartridge retainer portion of graft inserter assembly of FIG. 58.

FIG. 60 illustrates an exploded view of a cartridge retainer 502 illustrated in FIG. 59. The retainer 502 comprises a cartridge retainer housing 522 with a rack gear 523 fixed to the housing with locator pins 531 and fasteners 530. Releasable lock 514 is mounted to housing 522 within lock port 535 and comprises a lock plunger 532, plunger biasing member 533 here in the form of a spring, and a release knob 534. The spring biases the plunger towards interfering with lock recess 513 of chute housing 504 to secure it within retainer housing 522 until surgeon desires to remove it.

Figure 61:
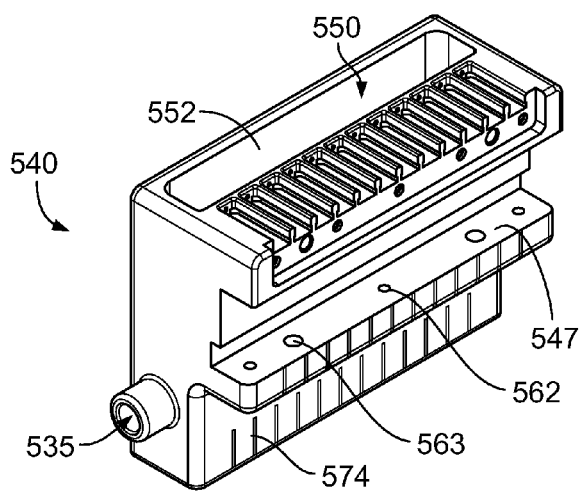
FIG. 61 is a bottom perspective view of a cartridge retainer housing body.
Figure 62:
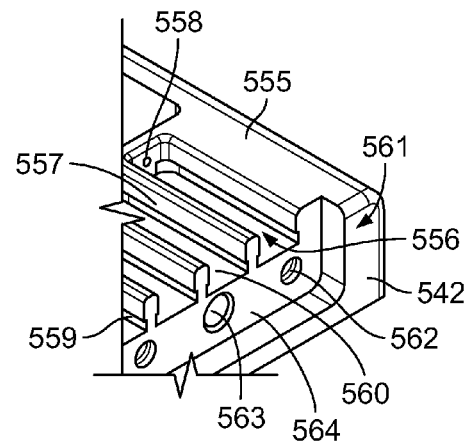
FIG. 62 is a bottom perspective close up view of chute door recesses of cartridge retainer housing body.
Figure 63:
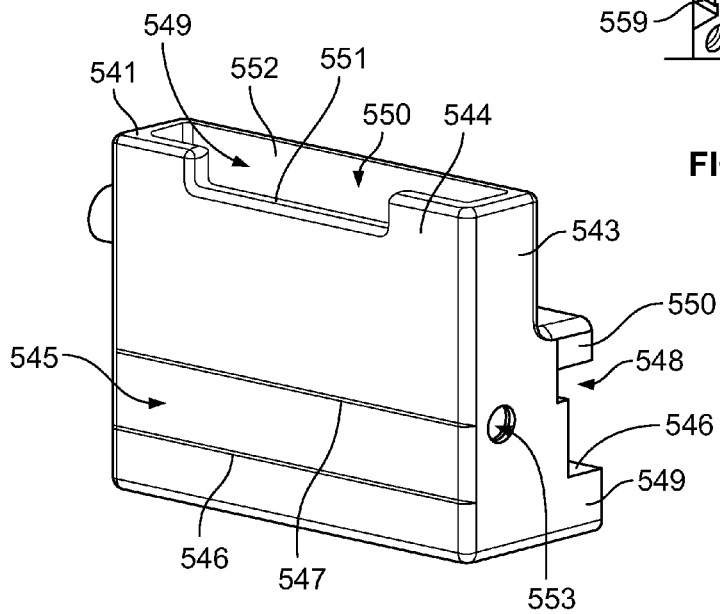
FIG. 63 is a rear perspective view of a cartridge retainer housing body.

The cartridge retainer housing 522 is further illustrated in FIG. 61-63. The housing comprises a body 540 with top face 541, front face 542, opposed side faces 543, rear face 544, and bottom face 555. Linearly cut into the rear face 544 is rear guide recess 545 bounded by a lower guide wall 546 and an upper guide wall 547. Similarly, cut into the front face 542 is front guide recess 548 defining an upper foot 550 and lower foot 549. The front guide recess 548 is bounded by a lower guide wall 546 and an upper guide wall 547. A cartridge aperture 550, bounded by boundary walls 552, extends from the top face 541 through the body 540 and bottom face 555 and is configured in size and profile to house graft cartridge 501. A handle recess 549 is cut through the rear face 544 and top face 541. It is here cartridge handle 506 resides and stop surface 551 abuts handle 506 when cartridge 501 is fully seated within the cartridge aperture 550. On side face 543 is auxiliary port 553 with plug 554.

Cut into front face 542 and bottom face 555 are chute door recesses 556 to provide housing of chute doors 527. Base wall 560 and containment walls 557 guide the chute doors 527 down a linear path and hold the doors within the recesses 556. At the end of the recesses 556 is pin aperture 558 to hold one end of door pin 524. Each chute door recess 556 is separated by a chute wall 559. Also cut into front face 542 and bottom face 555 is chute plate recess 561 for housing of chute plate 528. Located on base wall 564 of recess 561 is locator pin aperture 563 and threaded hole 562. Similarly, located on upper guide wall 547 are pin apertures 563 and threaded hole 562 for placement of rack gear 523 and securement with fasteners 529.

Figure 64:
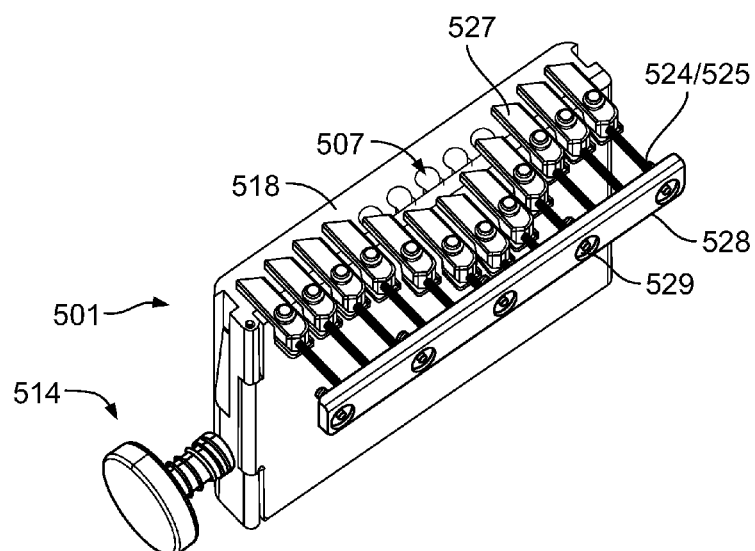
FIG. 64 is a bottom perspective view of the graft inserter assembly with selected portions removed to illustrate the functional interaction between the chutes and chute doors.
Figure 65A:
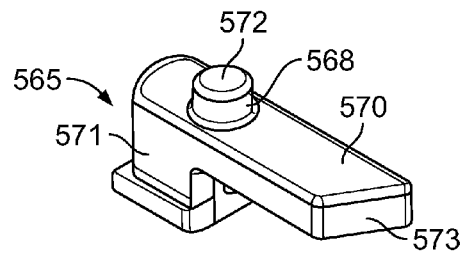
FIG. 65A is a bottom perspective view of a chute door.
Figure 65C:
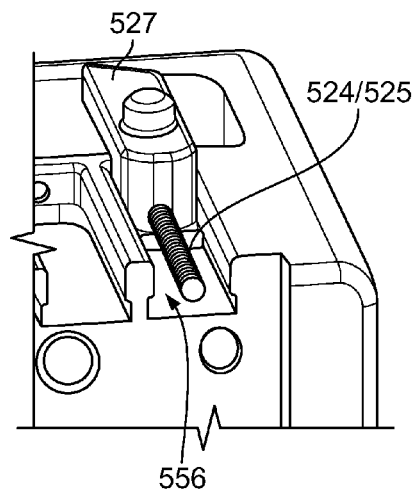
FIG. 65C is a close-up perspective view of a chute door residing in a chute door recess.
Figure 65B:
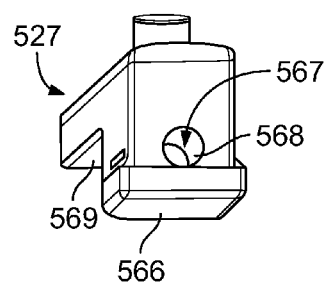
FIG. 65B is a rear perspective view of a chute door.
Figure 70:
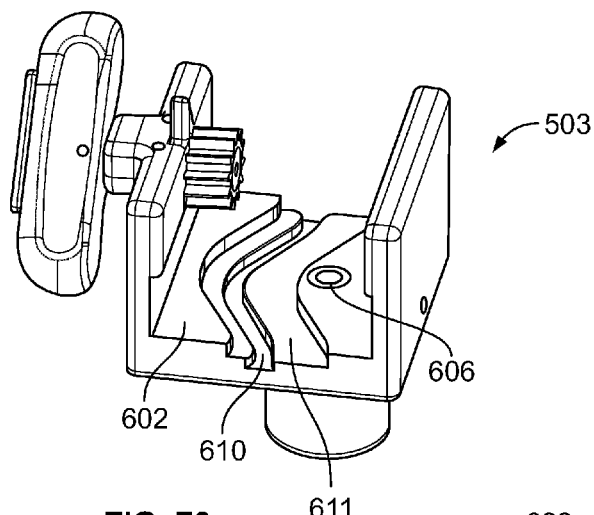
FIG. 70 is a top perspective view of a graft delivery guide portion of the graft inserter assembly.

As illustrated in FIG. 65C, chute doors 527 reside within the chute door recesses 556. The chute door 527 in this embodiment comprises an L-shaped body 565 with enlarged head 566 (FIGS. 65A & 65B). The chute door 527 is configured to slide along door pins 524 and resides between base wall 560, chute wall 559, and containment wall 557. The door 527 comprises a pin aperture 567 for passage of door pin 524 and a counter bore 568 to house end of biasing member 525. Chute door 527 further comprises a pair of opposing side walls 571, and bottom wall 570. Graft face 569 of chute door 527 seals chutes 507 during operation until the chute door is retracted for graft removal. Retraction of individual chute door is controlled by retraction face 573 which is sloped and rides in high door groove 611 of graft delivery guide 503 (FIG. 70) and boss face 568 of boss 572 rides in low door groove 611. Portions of this mechanism are illustrated in FIG. 64 wherein a portion of the chute doors 527 are retracted therein permitting release of graft (may be assisted by a chute plunger), and others are fully covering of chutes 507.

Figure 69:
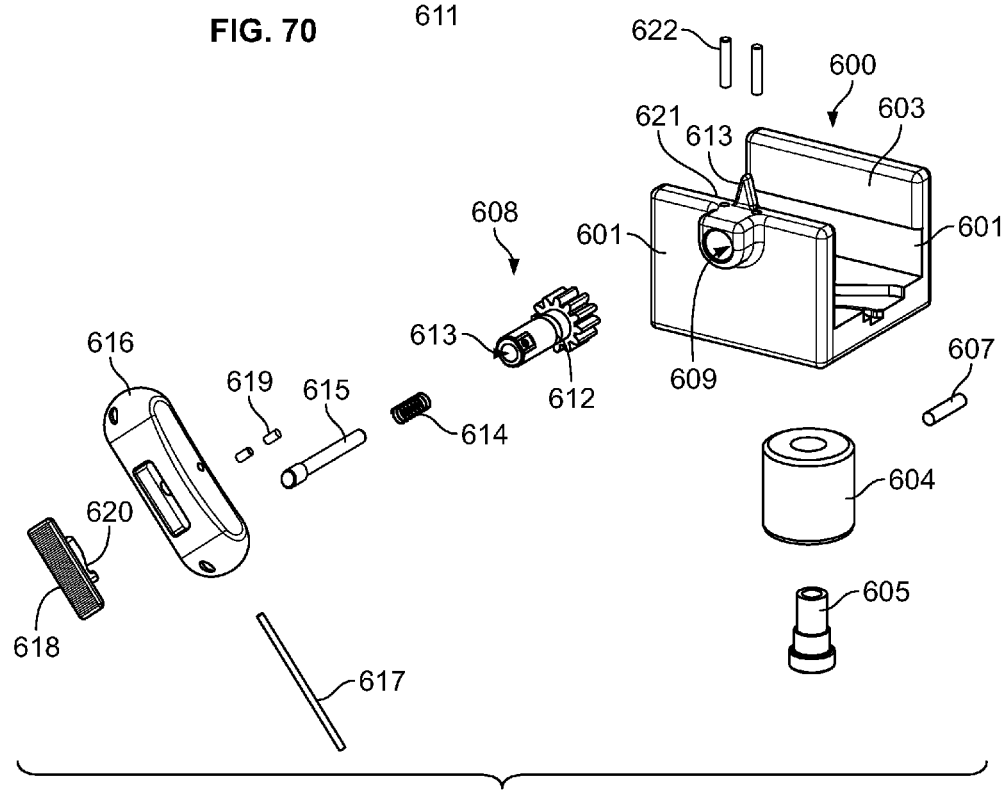
FIG. 69 is an exploded view of a graft delivery guide portion of the graft inserter assembly illustrated in FIG. 58.
Figure 72:
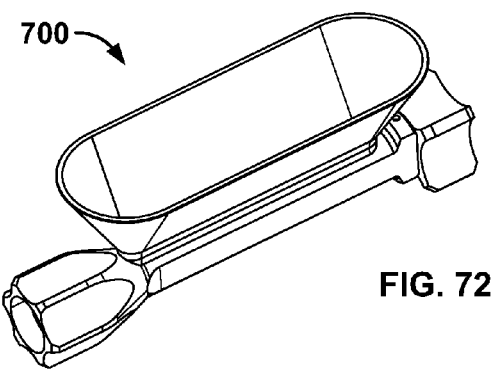
FIG. 72 is a top perspective view of a graft funnel.

FIG. 69 illustrates an exploded view of an exemplary embodiment of a graft delivery guide portion 503 of graft inserter 500. The guide portion 503 comprises a coupler 600 with a U-shaped body configured to hold cartridge retainer 502 on a base wall 602 and two opposing upright walls 601. Projecting inward from each upright wall 601 is capture wall 603. One capture wall 603 is configured to be received within the rear guide recess 545, and the other within the front guide recess 548 wherein cartridge retainer 502 is captured within coupler 600.

At the bottom of the U-shaped body is inserter tube 604 with cannulated fastener 605 configured to fix tube 604 to coupler 600 by threads on fastener 605 (not shown) threading into coupler aperture 606. Fixing pin 607 prevents release of inserter tube 604 from coupler 600. Pinion gear 608 resides in pinion aperture 609 and is secured in place by pins 622 about pinion shaft groove 612 when pins are pressed into pin holes 621. Pinion gear 608 comprises a locking aperture 613 extending therethrough for housing locking pin 615. Pinned to the end of the shaft of pinion gear 608 is handle 616 using pins 619.

The handle 616 comprises a sliding lock button 618 pinned to handle 616 utilizing pin 617. Sliding lock button 618 comprises a sloped activation surface 620 configured to engage locking pin 615 wherein when button 618 is slid in one direction, activation surface 620 will cause locking pin 615 to travel towards cartridge retainer 502 and held within one selector hole 536 of cartridge retainer housing 522 therein locking it in position. When button 618 is slid in the opposite direction, a gap is created between activation surface 620 and locking pin 615 wherein spring 614 will cause locking pin 615 to be removed from selector hole 536. In this 'unlocked' position, the cartridge retainer housing 522 is free to translate parallel to upright walls 601. Indicator 613 aligns with indicia 574 to indicate the specific chute 507 aligned with graft port 623 of cannulated fastener 605.

Figure 71:
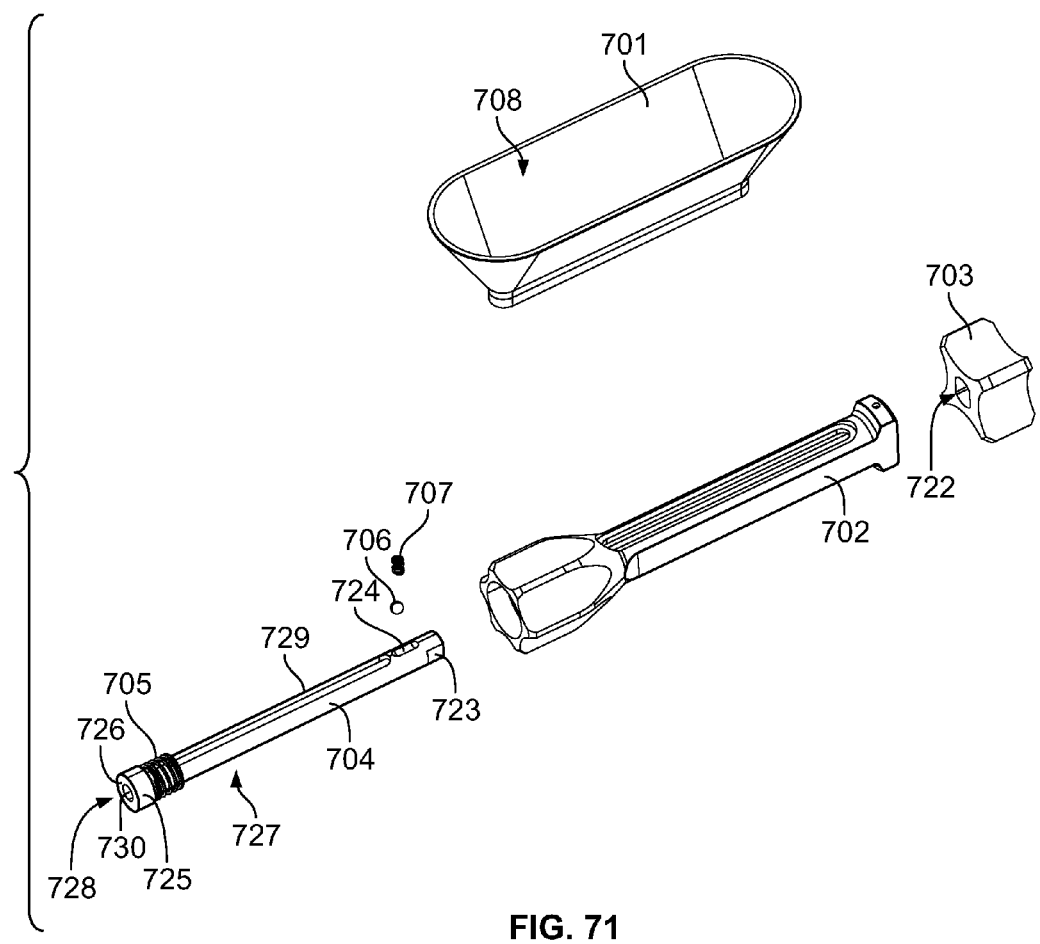
FIG. 71 is an exploded view of a graft funnel.
Figure 76:
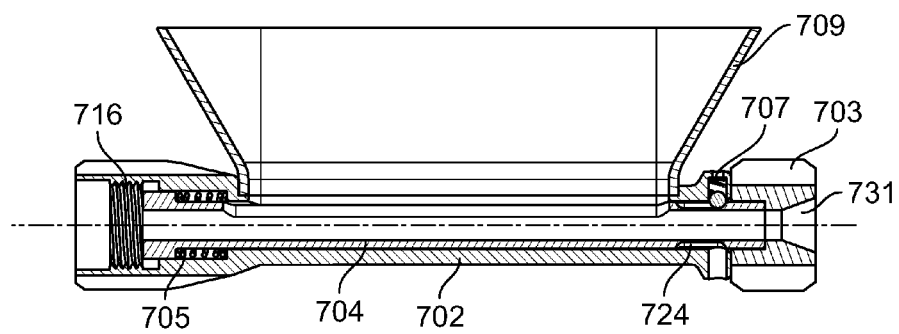
FIG. 76 is a cross-sectional view of the graft funnel illustrated in FIG. 72.
Figure 73:
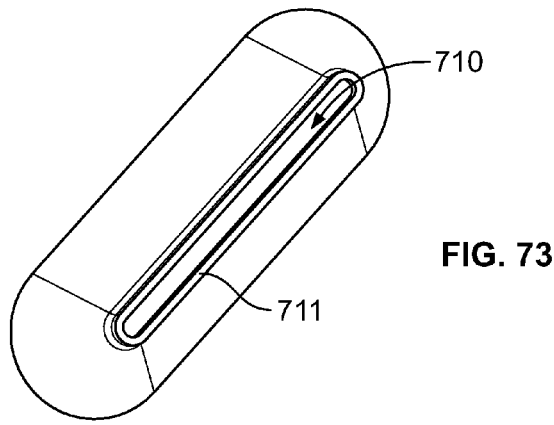
FIG. 73 is a bottom perspective view of a funnel portion of a graft funnel.
Figure 74:
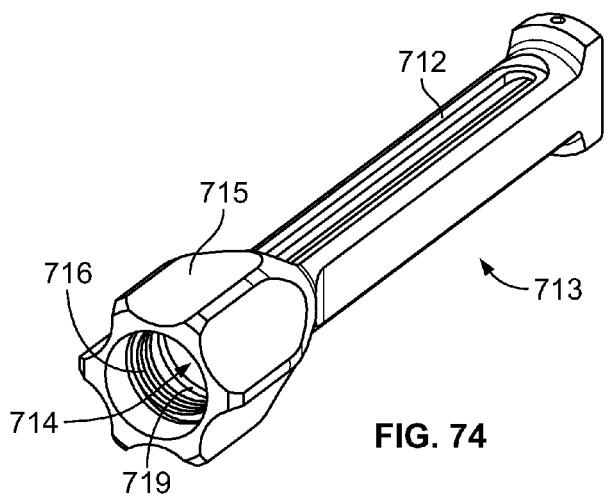
FIG. 74 is distal perspective view of a collector tube portion of the graft funnel illustrated in FIG. 72.
Figure 75:
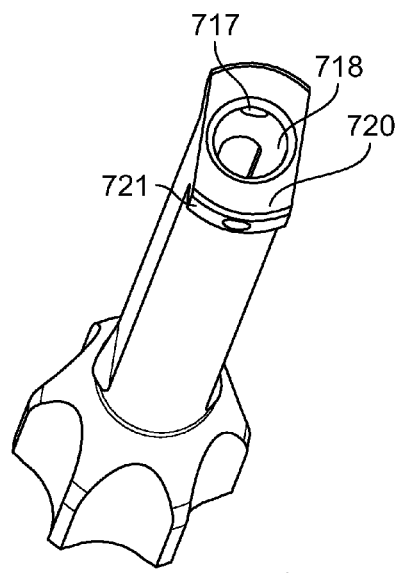
FIG. 75 is a proximal perspective view of a plunger tube of the graft funnel illustrated in FIG. 72.

As an alternative the graft inserter assembly 500, a graft funnel 700 is illustrated in FIGS. 71-76. FIG. 71 illustrates an exploded view of graft funnel 700. It comprises funnel 701, collector tube 702, plunger tube 704, sealing spring 705, ball 706, detent spring 707, and rotation knob 703. Graft funnel 700 comprises a broad open mouth 708 with inclined funnel walls 709 leading to an elongated funnel outlet 710. Outlet fitting 711 is configured for fit and secured in funnel inlet 712 of collector tube 702. The collector tube 702 comprises a tubular elongated body 713 with central aperture 714 along entire length of body 713 defining inner surface 718. Proximal to threads 716 is spring wall 719 serving as a fixation surface for spring 705. On outer surface of the collector tube at the distal end is grip 715 configured with ribs, knurling or other feature to ease user insertion of funnel 700 on the inserter. At the proximal end are opposing ears 721 with a blind hole 717 drilled from one side of the ear to house a ball detent mechanism 706,707 cooperating with plunger tube 704. Proximal face 720 faces rotation knob 703.

Plunger tube 704 comprises an elongated body 727 with central aperture 728 defining inner collector wall 730. Aperture 728 is sized to pass plunger type expansion rod for pushing graft toward spacer 100. At the distal end is enlarged head 725 terminating with inserter face 726. Graft inlet window 729 provides for passage of graft material from funnel 701 into central aperture 728. Proximal to graft inlet window 729 is an elongated detent groove 724 for cupping ball 706 that provides a small amount of translation of plunger tube 704 within collector tube 702. An opposing detent groove 724 is mirrored on opposing side of plunger tube 704. This ball detent system with elongated not only holds plunger tube 704 within collector tube 702, it also provides the users a means to quickly align the graft inlet window 729 with funnel outlet 710 to provide for graft placed into funnel 701 to flow into and fill central aperture 728 of plunger tube 704. Knob 703 comprises central aperture 722 having aperture walls configured to act on torsion faces 723 of plunger tube 704. A 180 degree turn of knob 703 by the user will in turn rotate plunger tube 704 to opposing ball detent groove 724 therein sealing off the central aperture 728 of plunger tube 704. Knob 703 further comprises a widened aperture 731 at its proximal end through which expansion rod style plunger, as described earlier, is utilized to push the graft housed in the plunger tube 704, through the fixation tube 303 and into graft aperture 122.

Figures 77, 78, 79:
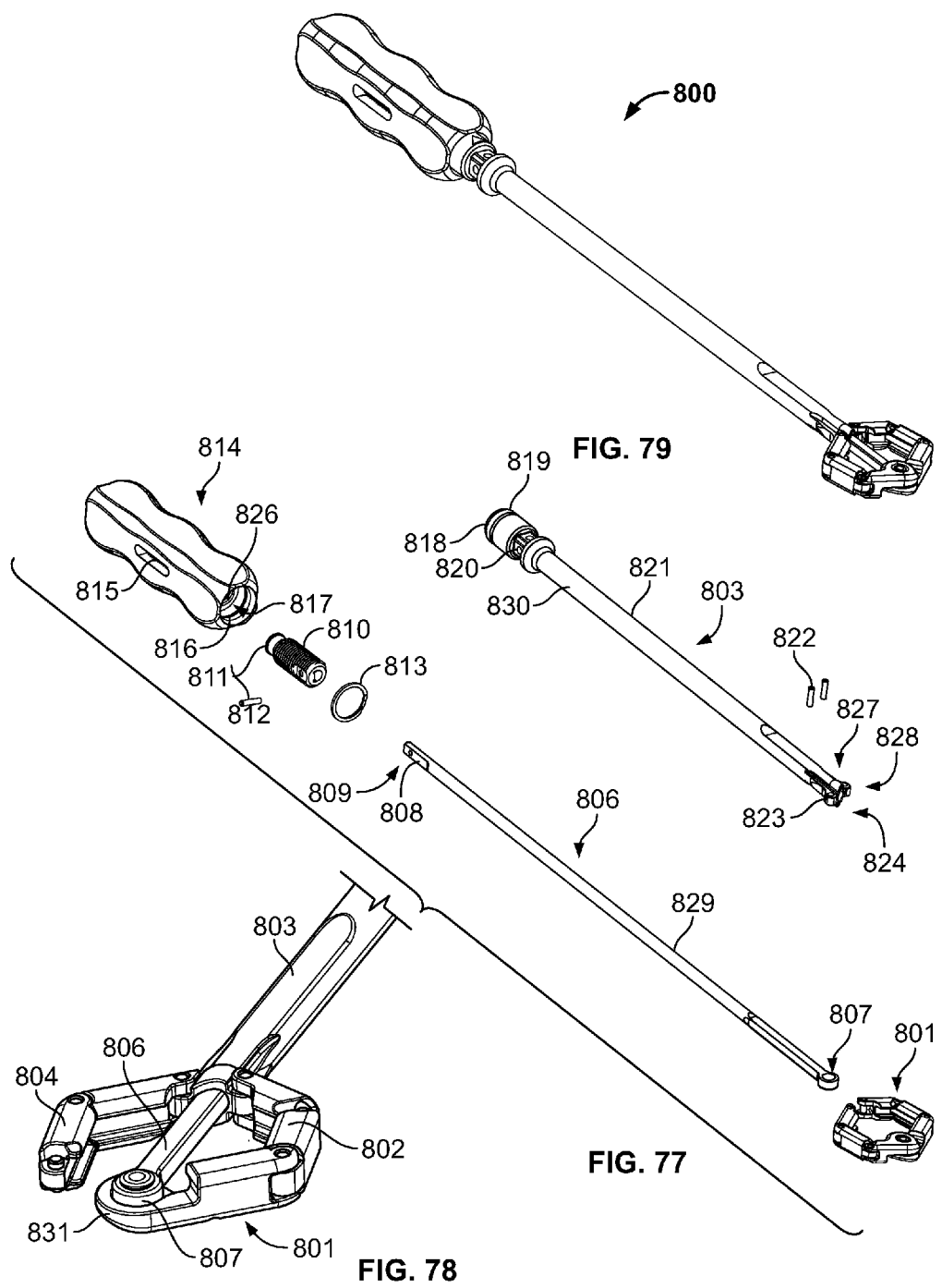
FIG. 77 is an exploded perspective view of an exemplary embodiment of the spacer template instrument illustrated in FIG. 79.
FIG. 78 is a close-up view of template spacer portion of the spacer template instrument illustrated in FIG. 79 with a link removed for viewing of expansion rod coupler.
FIG. 79 is a front perspective view of an exemplary embodiment of a spacer template instrument.

FIGS. 77-79 illustrate spacer template 800. Individual template instruments 800 correspond to specific spacer 100 sizes and are used as a quick method of validating the fit of a spacer 100 prior to implantation in the intervertebral space. Template 800 comprises a template spacer 801 further comprised of a series of pinned template links 802 generally replicating links 116-121 of spacer 100 with a few differences. One difference is teeth 108 on spacer 100 are absent and replaced with a smooth surface 804 to provide eased insertion and removal of template 800 in and out of the intervertebral space. Windows 171 extending through inner surface 172 of select links may be removed. In addition, the functional components of coupler 206 are now integrated into expansion rod 806 and positioner gears 207 and 209 are removed. The functionally equivalent MD and LD links 118, 110 in the template spacer have been modified accordingly to house coupler 807 of expansion rod 806.

Expansion rod 806 comprises an elongated body 829. The distal end of the rod 806 flattens into coupler 807 generally comprising a round disc with central aperture sized to house a fastener similar to fastener pivot assembly 200 used to secure links and coupler together. Located on the proximal end of expansion rod 806 are torsion features, here in the form of a male flat 808, to inter-attach rod 806 within corresponding female flat 825 within expansion drum 810. Pin 812 secures drum 810 to rod 806 through pinhole 809. Located on the outerbody of expansion drum 810, preferably at the proximal end is indicator 811 that is viewable through window 815 of handle 814 to monitor expansion progress of template spacer 801. The outerbody of expansion drum 810 comprises threads complementing threads 826 within drum aperture 817. At the distal end of drum aperture 817 is retainer groove 816 sized to house a portion of spring retainer ring 813.

Control tube 803 comprises an elongated body 821 with central rod aperture 824 extending therethrough and sized to house sliding expansion rod 806 therein. At the proximal end of control tube 803 is retainer groove 819 formed within control tube head 818. The retainer groove 819 is also configured to house a portion of spring retainer ring 813 wherein the ring holds handle 814 to control tube head 818 yet provides for rotational movement therebetween. Just below head 818 are torsional flats 820 for attachment of a counter torque device such as an open end wrench or similar device. At the distal end of control tube 803 is link control head 828. The head comprises one or more bosses 823 each having an integrated pin aperture 827. The control head 828 is held with pins 822 to the corresponding template spacer links 802. The corresponding insertion link 115 is integrated into control tube 803 of spacer template 800 since the template links are not required to be released from the template instrument. However, in alternative embodiments, it is contemplated that control tube 803 may be configured to be releasable from various spacer templates 800. The outer surface of the control tube may include indicia 830 to indicate instrument orientation (i.e. medial or lateral). By rotation of handle 814, spacer template 800 is capable of transforming template spacer 801 between insertion and expanded configurations.

In an exemplary embodiment, the spacer 100 and method are configured for a transforaminal surgical approach. The patient is placed on a radiolucent surgical table in the prone position. A retractor is positioned over the pre-determined operative level. Anatomic landmarks are identified followed by initial incisions localized at the disc space using fluoroscopy in the anterior/posterior (A/P) and lateral views. A radiograph is taken and additional radiographs are taken at any time at the surgeon's discretion.

The patient's pedicles are targeted above and below the affected level and the location of each is marked. A skin incision is made between the pedicle markings with sizing appropriate for the retractor used. Using finger dissection, a cobb, or curette, tissue is released from the facet joint at the affected level. Fascia or tissue at the pedicles preventing placement of the retractor is removed. The retractor is inserted over the facet joint and positioned and secured to be parallel to the disc space for the proper medial exposure trajectory.

The surgeon then performs a conventional facetectomy and decompression followed by annulotomy and discectomy. Using any combination of pituitary rongeurs, disc cutters, endplate scrapers, curettes, and rasps, the surgeon removes as much disc material from the disc space as possible. A variety of angled instruments are then used to prepare the contralateral/posterior and ipsilateral/anterior regions of the disc. The endplates are prepared to remove cartilage and expose bleeding subchondral bone.

Figure 80:
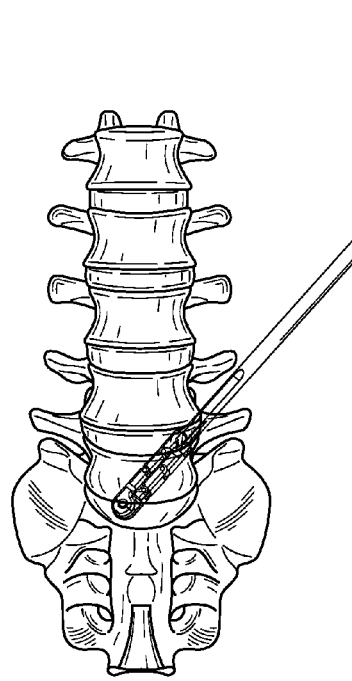
FIG. 80 is an anterior view of the spacer template inserted in the disc space.

An appropriately sized spacer template 800, with template spacer 801 in the collapsed configuration is selected and inserted down the surgical path at an oblique angle with the "MEDIAL" and "LATERAL" markings 830 on the instrument in the correct orientation relative to the patient's spine. The template is inserted until the distal tip 831 of spacer 801 abuts the annulus at the anterior/contralateral region of the disc space (FIG. 80). Using lateral fluoroscopy, the distal tip 831 is confirmed to be abutting the anterior annulus. Using anterior-posterior (A/P) fluoroscopy, the distal tip is checked to assure it abuts the projected medial border of the contralateral pedicle. If necessary, a surgical mallet is used to impact the proximal end of handle 814 until it reaches the desired location.

Figure 81:
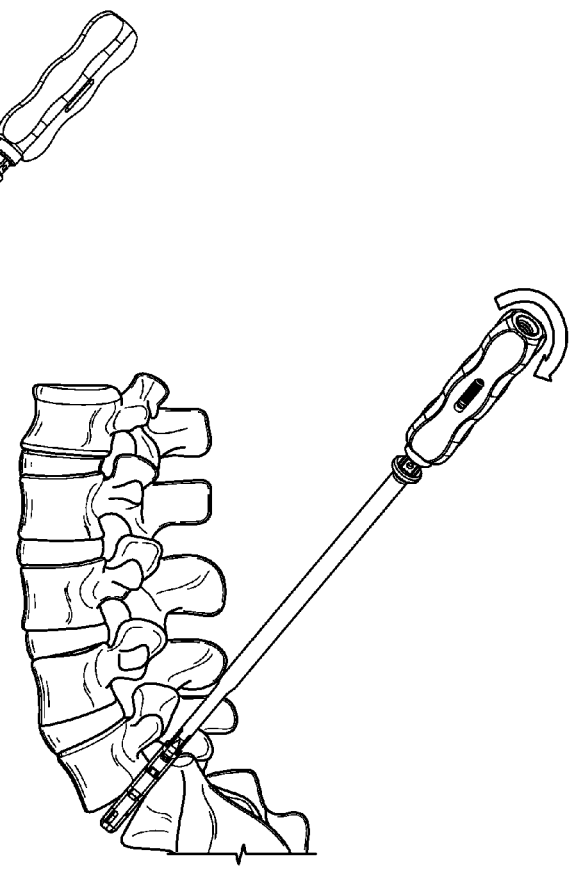
FIG. 81 is a lateral view illustrating expansion of the spacer template.
Figure 82A:
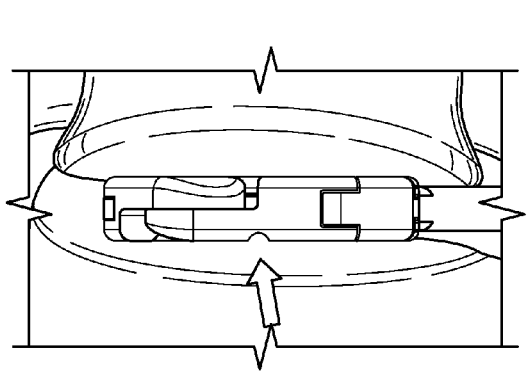
FIG. 82A illustrates from an anterior view notch alignment indicating full expansion of the spacer template.
Figure 82B:
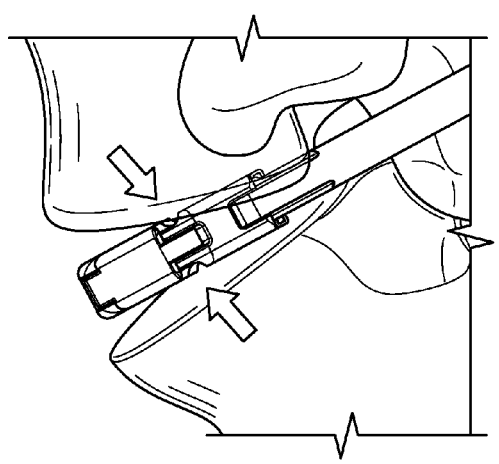
FIG. 82B illustrates from a lateral view notch alignment indicating full expansion of the spacer template.

Under A/P and lateral fluoroscopy, the handle 814 of template 800 is advanced by clockwise rotation to expand the template (FIG. 81). Full expansion can be confirmed via fluoroscopy as the notches on the expanded template will be coincident in the direct A/P and direct lateral views as indicated in FIG. 82. Full expansion can be confirmed via visual indicator on the footprint template handle as illustrated in FIG. 83.

The spacer template 800 is transitioned prior to removal by rotating the template handle counter-clockwise until it returns to a collapsed insertion configuration. The surgeon will choose an alternate sized spacer template if necessary until the proper spacer template size has been determined using tactile feel and fluoroscopy. Additional disc tissue may be removed as needed to facilitate full expansion.

An appropriately sized paddle sizer is then chosen as illustrated in FIG. 84. A T-handle is attached to the end of the sizer and inserted into the disc space using an oblique trajectory. Appropriate "MEDIAL" and "LATERAL" instrument markings are followed if the sizer is rotated to height relative to the patient. The sizing iterations are continued until the proper height and lordosis have been determined using tactile feel and lateral fluoroscopy.

An appropriately sized spacer 100 is then chosen and attached to the spacer inserter 300 by aligning the control arms 350 with control guide 144 on insertion link 115 and advancing together. Lockwheel 348 is rotated (clockwise) until fixation tube 303 threads 372 advance into aperture 149 and instrument stop surface 156 on insertion link 115 is tight against link face 344 on control frame 301 as illustrated in FIG. 85.

Figure 86:
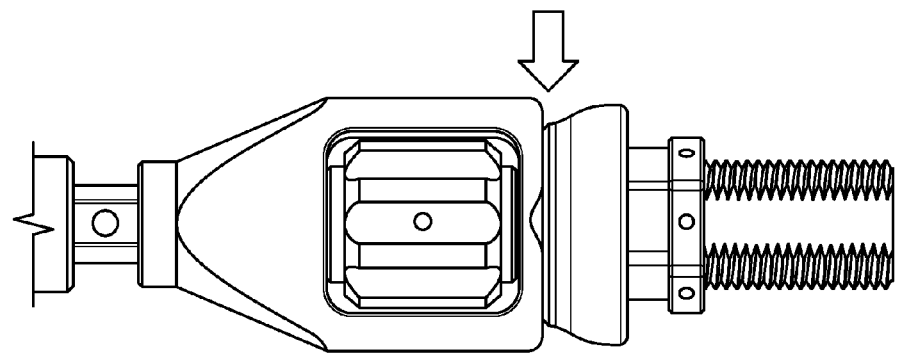
FIG. 86 illustrates pre-setting of the handle collar assembly on the control frame by the arrow pointing to no gap between rotating collar and inserter.
Figure 87A:
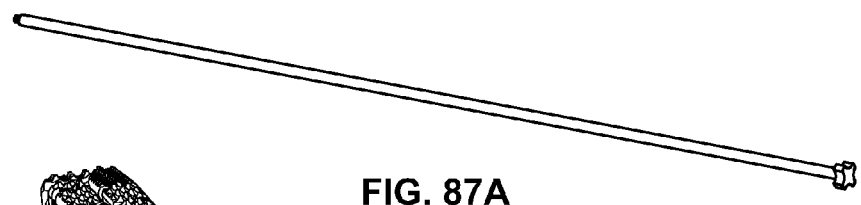
FIG. 87A illustrates an expansion rod.
Figure 87B:
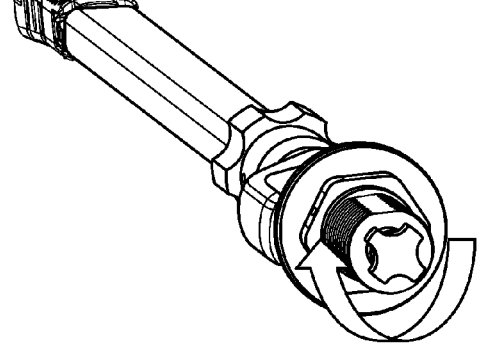
FIG. 87B illustrates threading of the expansion rod through inserter and into coupler link.
Figure 88:
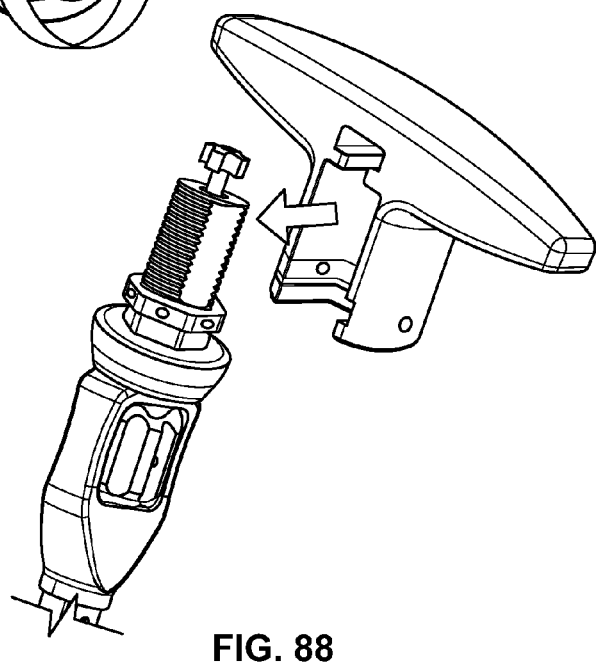
FIG. 88 illustrates mounting expansion handle over the handle collar.

Handle collar assembly 302 is advanced on collar neck 334 of control frame 301 until distal stop face 355 abuts bulb portion 347 of control frame 301 as illustrated in FIG. 86. An optional expansion limiter 305 may be attached to limiter neck 336. An appropriately sized expansion rod 304 corresponding to the spacer 100 size is selected. Using enlarged head 310, and leading with threaded boss 375, the expansion rod 375 is advanced through working aperture 332 of control frame 301 and threaded (clockwise) into coupler aperture 242 of coupler 206 until stop surface 243 abuts stop surface 376 on expansion rod 304 as illustrated in FIG. 87. Expansion handle 306 is then mounted over outer drive collar 367 while spacer 100 remains in the insertion configuration as illustrated in FIG. 88.

Figure 89:
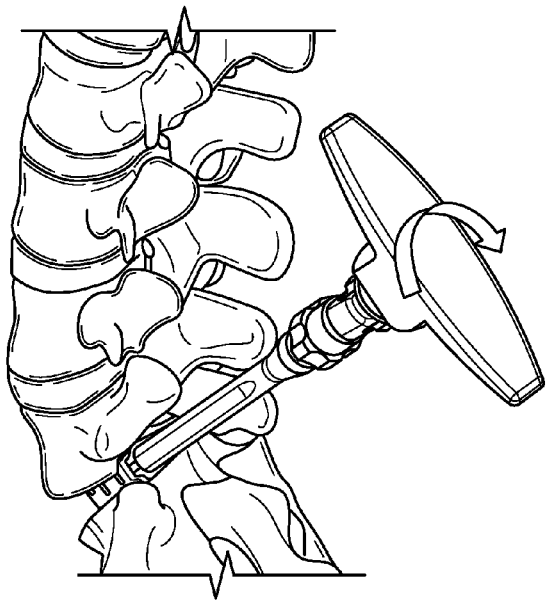
FIG. 89 illustrates rotation of the expansion handle to transition spacer to expanded configuration.
Figure 90:
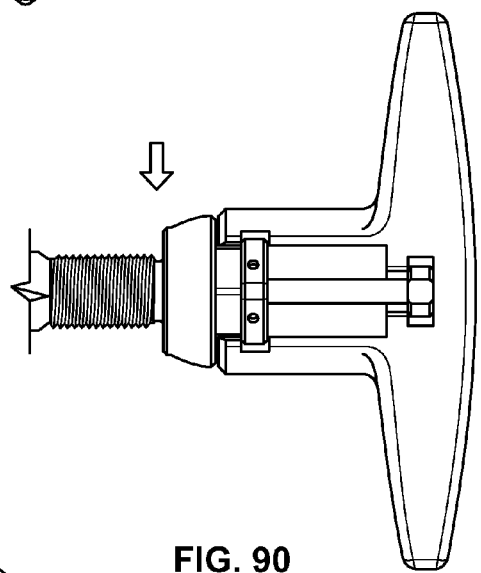
FIG. 90 illustrates confirmation of full spacer expansion as indicated by indicia on control frame by the arrow pointing to green indicator appears below collar.
Figure 91:
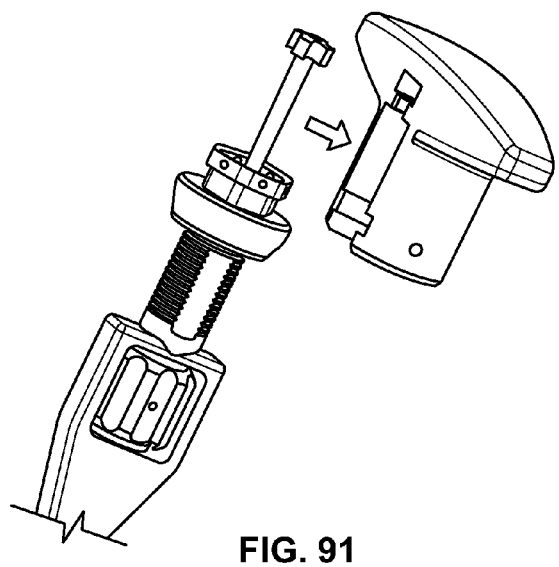
FIG. 91 illustrates removal of expansion handle from handle collar.

Spacer 100 is then inserted down the surgical path into the disc space using an oblique trajectory while ensuring that the "MEDIAL" and "LATERAL" indicia 393 are in the correct orientation relative to the patient. Under fluoroscopy, the implant is expanded through rotation of the expansion handle as illustrated in FIG. 89, while a distal directed force is maintained during expansion and the anterior aspect of the implant in monitored via fluoroscopy to assure it remains in the desired location. Tactile resistance may be felt when the implant is in its fully-expanded state. Full expansion can be confirmed via fluoroscopy as well as by visual indicator 351 on the implant inserter as seen in FIG. 90. Radiographs may be taken to confirm correct placement of spacer 100 in the intervertebral space. If desired, handle 306 may be derotated to return to the insertion configuration for spacer 100 removal or readjustment. When fully collapsed, the rotating collar on the inserter will be fully seated distally. Once proper placement is achieved, expansion handle 306 is removed from spacer inserter 300 by releasing handle lock 307 (if so equipped) and sliding handle 306 off as seen in FIG. 91.

Figure 92:
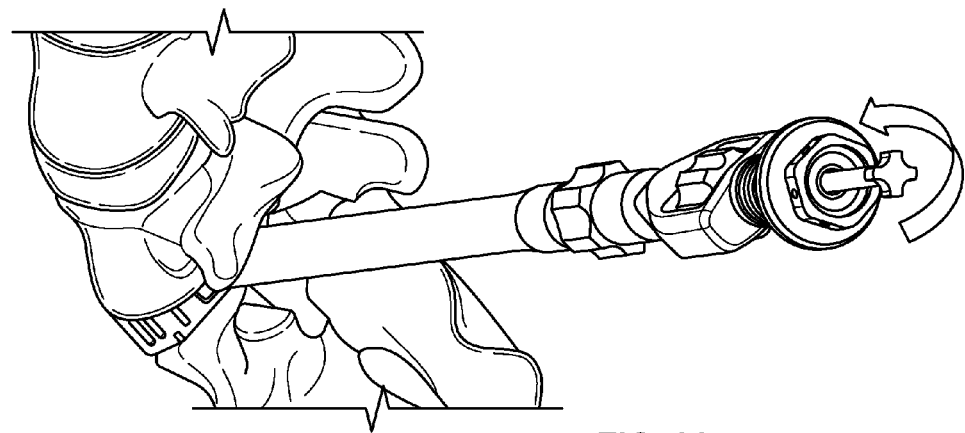
FIG. 92 illustrates derotation of expansion rod to release it from the coupler for removal.
Figures 93A, 93B:
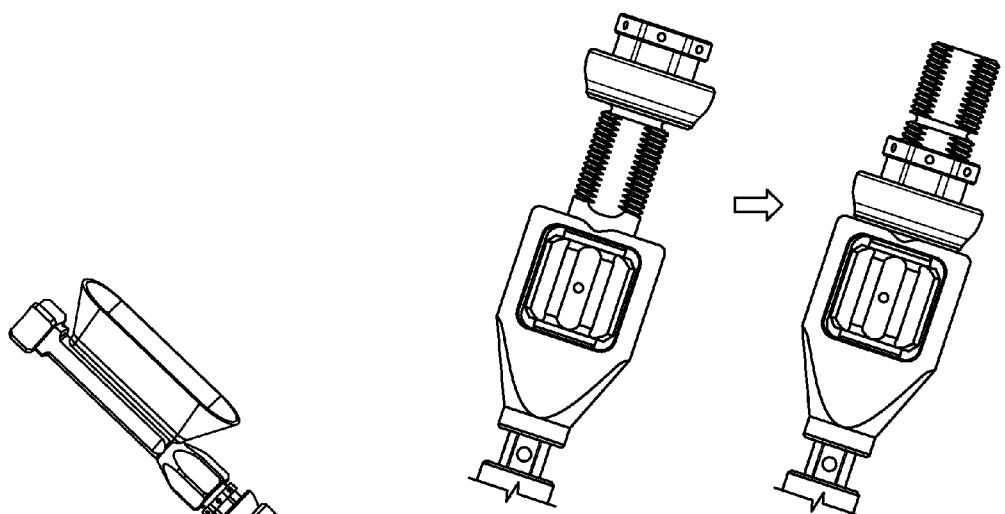
FIG. 93A and FIG. 93B illustrate re-setting the handle collar assembly.
Figure 94:
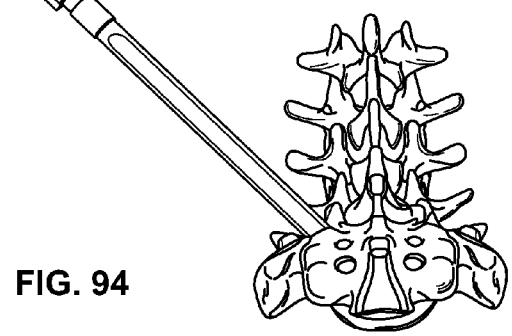
FIG. 94 illustrates the graft funnel inserted on the inserter.

The expansion rod 304 is released from coupler 206 through derotation of enlarged head 310 as illustrated in FIG. 92. The handle collar assembly 302 is rotated until distal stop face 355 abuts bulb portion 347 of control frame 301 as illustrated in FIG. 93. Graft funnel 700 as illustrated in FIG. 94, or graft inserter assembly 500 may now be attached to collar neck 334 (limiter neck 336 may be absent in some embodiments).

Figure 95:
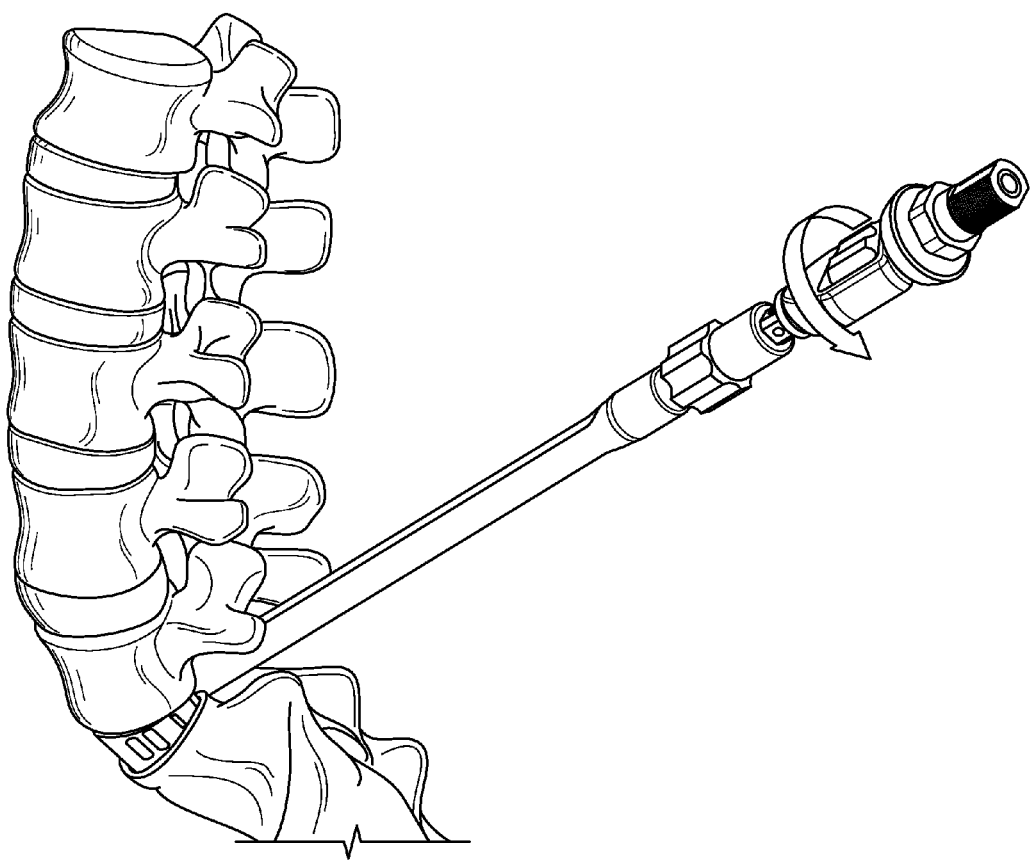
FIG. 95 illustrates derotation of the lockwheel for removal of the instruments from the spacer.

The graft funnel 700 is attached by advancing threaded 716 aperture of collector tube 702 over collar neck 334 until snug. The funnel 701 is filled with autograft guided into the central aperture 728 of plunger tube 704 until full. Using knob 703, the plunger tube 704 is rotated until ball detent engages at 180 degrees. An expansion rod style plunger is advanced down widened aperture 731 pushing graft into graft aperture 122 of spacer 100. This action is repeated until graft aperture is filled to the desired level. The funnel 700 is then removed from the implant inserter followed by removal of the implant inserter by rerotation of lockwheel 348 therein releasing spacer inserter 300 from spacer 100 as illustrated in FIG. 95.

The retractor and all instruments are then removed from the patient. The surgeon my choose to take an A/P fluoroscopy image of the operative site with the C-Arm at 0 degrees and a lateral image with the C-Arm at 90 degrees. The applicable steps from above are utilized if additional implants are desired at an additional operative level as chosen by the surgeon.

In an alternative method to using graft funnel 700, graft delivery guide 503 is attached by advancing inserter tube 604 over collar neck 334 and tightening until snug. The cartridge retainer is set on a flat sterile surface against cartridge handle 506 with door 505 facing up. Door 505 is opened and bone graft is spread across chutes 507. Door 505 is closed once chutes 507 are filled with desired amount of bone graft. Lock 514 is withdrawn and cartridge retainer 501 is inserted into cartridge aperture 550 of the cartridge retainer housing 502 and secured by releasing lock 514.

The cartridge retainer housing 502 with cartridge retainer is then loaded into the right side of graft delivery guide wherein rear guide recess 545 and front guide recess 548 are captured between capture walls 603. With sliding lock button 618 unlocked, handle 616 is rotated counter clockwise causing pinion gear 608 to advance rack gear and cartridge retainer 502 across coupler 600 until a selected chute aligns with indicator 613. Sliding lock button 618 may be engaged to secure cartridge retainer in place. The chute door 527 aligned with indicator 613 at center of coupler 600 is opened by walls of curved low door groove 610 and high door groove 611 acting on retraction face 573 and boss face 568 against biasing member 525.

A fixation rod style plunger is used to push the bone graft for said open chute through graft port 623 and fixation tube 303 into graft aperture 122. The cartridge retainer 502 is advanced by the pinion gear 608 to the next chute and the plunger process is repeated until a desired amount of graft is pushed into graft aperture 122. The graft inserter assembly and spacer inserter may then be removed.

While the present invention has been shown and described in terms of preferred embodiments thereof, it should be understood that this invention is not limited to any particular embodiment and that changes and modifications may be made without departing from the true spirit and scope of the invention as defined in the appended claims.

What is claimed is:
1. An intervertebral spacer, comprising:
   a first side having a proximal end and a distal end and comprising a first plurality of links joined by a first plurality of joints;
   a second side having a proximal end and a distal end and comprising a second plurality of links joined by a second plurality of joints;

a proximal end including an insertion link having an aperture dimensioned to receive an insertion tool, said insertion link joined to proximal ends of the first side and the second side;

a distal end including a coupling assembly for receiving a portion of the insertion tool;

a first support face configured to contact a first vertebral body endplate; and a second support face opposite said first support face configured to contact a second vertebral body endplate, wherein said intervertebral spacer has an insertion configuration in which the spacer is elongated and the first side and the second side are linear and an axis of insertion is parallel to a longitudinal axis of the intervertebral spacer, and a fully expanded configuration in which the first side and the second side are displaced to define a graft aperture therebetween, and the intervertebral spacer has a hexagonal perimeter that is asymmetrical about the axis of insertion;

a positioner gear assembly housed in the distal end of the spacer, and configured to maintain the intervertebral spacer in an expanded configuration.

2. The intervertebral spacer of claim 1, wherein the intervertebral spacer is bisected by a first axis parallel to a sagittal plane when the spacer is in the fully expanded configuration within an intervertebral disc space.

3. The intervertebral spacer of claim 2, wherein the perimeter of the intervertebral spacer is symmetrical about the first axis.

4. The intervertebral spacer of claim 1, wherein at least one of the plurality of links of the first side includes a window.

5. The intervertebral spacer of claim 4, wherein at least one of the plurality of links of the second side includes at window.

6. The intervertebral spacer of claim 1, wherein the first side has a first height at the distal end and a second height at the proximal end and wherein the first height is greater than the second height.

7. The intervertebral spacer of claim 6, wherein the second side has a first height at the distal end and a second height at the proximal end and wherein the first height is greater than the second height.

* * * * *